US006924311B2

(12) United States Patent
Schulman et al.

(10) Patent No.: US 6,924,311 B2
(45) Date of Patent: Aug. 2, 2005

(54) METHODS FOR AFFECTING VARIOUS DISEASES UTILIZING LXR COMPOUNDS

(75) Inventors: Ira G. Schulman, San Diego, CA (US); Eric D. Bischoff, San Diego, CA (US); Rajendra K. Tangirala, San Diego, CA (US)

(73) Assignee: X-Ceptor Therapeutics, Inc., San Diego, CA (US)

( * ) Notice: Subject to any disclaimer, the term of this patent is extended or adjusted under 35 U.S.C. 154(b) by 0 days.

(21) Appl. No.: 09/982,544

(22) Filed: Oct. 17, 2001

(65) Prior Publication Data

US 2003/0073614 A1 Apr. 17, 2003

(51) Int. Cl.$^7$ .......................... A61K 31/18; A61K 49/00
(52) U.S. Cl. ....................... 514/601; 514/604; 514/585; 514/596; 514/352; 514/354; 514/529; 424/9.1; 564/52; 530/350
(58) Field of Search ................................ 514/600, 604, 514/585, 596, 352, 354, 529, 601; 564/52; 530/350; 424/9.1

(56) References Cited

U.S. PATENT DOCUMENTS

| | | | |
|---|---|---|---|
| 5,273,995 A | 12/1993 | Roth | 514/422 |
| 5,571,696 A | 11/1996 | Evans et al. | 435/69.1 |
| 5,607,967 A | 3/1997 | Friedman et al. | 514/461 |
| 5,639,616 A | 6/1997 | Liao et al. | 435/7.1 |
| 5,679,518 A | 10/1997 | Friedman et al. | 435/6 |
| 5,696,233 A | 12/1997 | Evans et al. | 530/350 |
| 5,710,004 A | 1/1998 | Evans et al. | 435/6 |
| 5,747,661 A | 5/1998 | Evans et al. | 536/24.1 |
| 5,869,284 A | 2/1999 | Cao et al. | 435/69.1 |
| 5,939,322 A | 8/1999 | Rodan et al. | 435/365 |
| 6,184,215 B1 | 2/2001 | Elias et al. | 514/182 |
| 6,277,976 B1 | 8/2001 | Enmark et al. | 536/23.5 |
| 6,316,503 B1 | 11/2001 | Li et al. | 514/604 |
| 2002/0072073 A1 | 6/2002 | Medina et al. | 435/7.1 |
| 2002/0116731 A1 | 8/2002 | Allen et al. | 800/18 |
| 2002/0177602 A1 * | 11/2002 | Piper | 514/291 |

FOREIGN PATENT DOCUMENTS

| | | | |
|---|---|---|---|
| WO | WO 95/13373 | 5/1995 | |
| WO | WO 96/05300 | 2/1996 | |
| WO | WO 96/21726 | 7/1996 | |
| WO | WO 97/28137 | 8/1997 | |
| WO | WO 98/32444 | 7/1998 | |
| WO | WO 99/18124 | 4/1999 | |
| WO | WO 99/27365 | 6/1999 | |
| WO | WO 00/34461 | 6/2000 | |
| WO | WO 00/37077 | 6/2000 | |
| WO | WO 00/54759 | 9/2000 | |
| WO | WO 00/66611 | 11/2000 | |
| WO | WO 00/78972 | 12/2000 | |
| WO | WO 01/03659 | 1/2001 | |
| WO | WO 01/03705 * | 1/2001 | A61K/31/655 |
| WO | WO 01/15676 | 3/2001 | |
| WO | WO 01/41704 | 6/2001 | |
| WO | WO 01/60818 | 8/2001 | |
| WO | WO 02/11708 | 2/2002 | |
| WO | WO 02/24632 | 3/2002 | |
| WO | WO 02/55657 | 7/2002 | |
| WO | WO 2004/058175 * | 7/2004 | |

OTHER PUBLICATIONS

Stulnig, Thomas M., et al. "Liver X Receptors Downregulate 11β–Hydroxysteroid Dehydrogenase Type 1 Expression and Activity", *Diabetes*, (2002), 51:2426–2433.

Cao, Guoqing, et al. "Antidiabetic Action of a Liver X Receptor Agonist Mediated By Inhibition of Hepatic Gluconeogenesis", *The Journal of Biological Chemistry*, (2000), 273(2):1131–1136.

Alberti. "Structural Characterisation of the Mouse Nuclear Oxysterol Receptor Genes LXRα and LXRβ" Gene 243:93–103 (2000).

Apfel. et al. "A Novel Orphan Receptor Specific for a Subset of Thyroid Hormone–Responsive Elements and Its Interaction with the Retinoid/Thyroid Hormone Receptor Subfamily" Mol. Cell. Biol. 14:7025–7035 (1994).

Auboeuf et al. "Tissue Distribution and Quantification of the Expression of mRNAs of Peroxisome Proliferator–Activated Receptors and Liver X Receptor–α in Humans" Diabetes 46:1319–1327 (1997).

Chen, et al. "Evidence That the Diabetes Gene Encodes the Leptin Receptor: Identification of a Mutation in the Leptin Receptor in db/db Mice" Cell 84:491–495 (1996).

Evans, et al. "Inhibition of Cholesteryl Ester Transfer Protein in Normocholesterolemic and Hypercholesterolemic Hamsters: Effects on HDL Subspecies. Quantity, and Apolipoprotein Distribution" J. Lipid Res. 35:1634–1645 (1994).

Gordon, et al. "High Density Lipoprotein As a Protective Factor Against Coronary Heart Disease" Am. I. Med. 62:707–714 (1977).

(Continued)

*Primary Examiner*—Jon Weber
*Assistant Examiner*—Chih-Min Kam
(74) *Attorney, Agent, or Firm*—Townsend and Townsend and Crew, LLP

(57) ABSTRACT

The present invention relates to methods for elevating high density lipoprotein (HDL) plasma levels, decreasing the absorption of dietary cholesterol in the intestine, decreasing the plasma level of low density lipoprotein (LDL), and increasing the conversion of cholesterol to bile acids, utilizing LXRβ selective agonists, usually without elevating the plasma levels of triglycerides. Also provided are methods of using such agonists to treat metabolic diseases alone or in combination with other active agents. Also provided are methods for decreasing hyperglycemia and insulin resistance methods for treating type II diabetes, and methods for treating type II diabetes and reducing the cardiovascular complications of type II diabetes, utilizing an LXR agonist. Further provided are methods for treating obesity and methods for treating the complications of obesity including type II diabetes, cardiovascular disease, hyperlipidemia, and hypertension, administering an LXRα-selective antagonist.

25 Claims, 15 Drawing Sheets

OTHER PUBLICATIONS

Havel et al. "Structure and Metabolism of Plasma Lipoproteins" in *Metabolic Basis of Inherited Disease*. 6$^{th}$ ed. 1989 pp. 1129–1138.

Janowski. "Structural Requirements of Ligands for the Oxysterol Liver X Receptors LXRα and LXRβ" PNAS 96:266–271 (1999).

Kannel, et al. "Cholesterol in the Prediction of Atherosclerotic Disease" Ann. Internal Med. 90:85–91 (1979).

Knowler, et al. "Obesity in the Pima Indians: Its Magnitude and Relationship with Diabetes" Am. J. Clin. Nutr. 53:1543–1551 (1991).

Laffitte et al "LXRs Control Lipid–inducible Expression of the Apolipoprotein E Gene in Macrophages and Adipocytes" PNAS 98(2):507–512 (2001).

Merck Manual, 16$^{th}$ ed. 1992 pp. 1039–1040.

Peet, et al. "Cholesterol and Bile Acid Metabolism Are Impaired in Mice Lacking the Nuclear Oxysterol Receptor LXRα" Cell 93:693–704 (1998).

Repa. "The Role of Orphan Nuclear Receptors in the Regulation of Cholesterol Homeostasis" Annu. Rev. Cell Dev. Biol. 16:459–81 (2000).

Repa et al. "Regulation of Mouse Sterol Regulatory Element–binding Protein–1c Gene (SREBP–1c) by Oxysterol Receptors, LXRα and LXRβ" Genes & Devel 14:2819–2830 (2000).

Repa et al. "Inhibition of Cholesterol Absorption and Regulation of ABC1–mediated Cholesterol Efflux by the RXR/LXR Heterodimer" Science 289:1524–1529 (2000).

Saito et al. "Frequent Association of Alternative Splicing of NER, A Nuclear Hormone Receptor Gene in Cancer Tissues" Oncogene 14:617–621 (1997).

Schultz et al. "Role of LXRs in Control of Lipogenesis" Genes & Development 14:2831–2838 (2000).

Seol et al. "Isolation of Proteins That Interact Specifically with the Retinoid X Receptor: Two Novel Orphan Receptors" Molec. Endo. 9:72–85 (1995).

Shinar et al"NER, A New Member of the Gene Family Encoding the Human Steroid Hormone Nuclear Receptor" Gene 147(2):273–276 (1994) (Abstract) at <http://www.ncbi.nlm.nih.gov> (visited Jan. 29, 2001).

Song et al. "Ubiquitous Receptor: A Receptor That Modulates Gene Activation by Retinoic Acid and Thyroid Hormone Receptors" PNAS 91:10809–10813 (1994).

Teboul "OR–1, A Member of the Nuclear Receptor Superfamily That Interacts with the 9–cis–retinoic Acid Receptor" PNAS 92:2096–2100 (1995).

Tobin. "Cross–Talk Between Fatty Acid and Cholesterol Metabolism Mediated by Liver X Receptor–α" Molecular Endocrinology 14(5):741–752 (2000).

Tobin et al. "Liver X Receptors as Insulin–mediating Factors in Fatty Acid and Cholesterol Biosynthesis" J. Biol. Chem. 277(12):10691–10697 (2002).

Venkateswaran et al. "Control of Cellular Cholesterol Efflux by the Nuclear Oxysterol Receptor LXRα" PNAS 97(22):12097–12102 (2000).

Willy, et al. "LXR, A Nuclear Receptor That Defines a Distinct Retinoid Response Pathway" Genes Dev. 9:1033–1045 (1995).

* cited by examiner

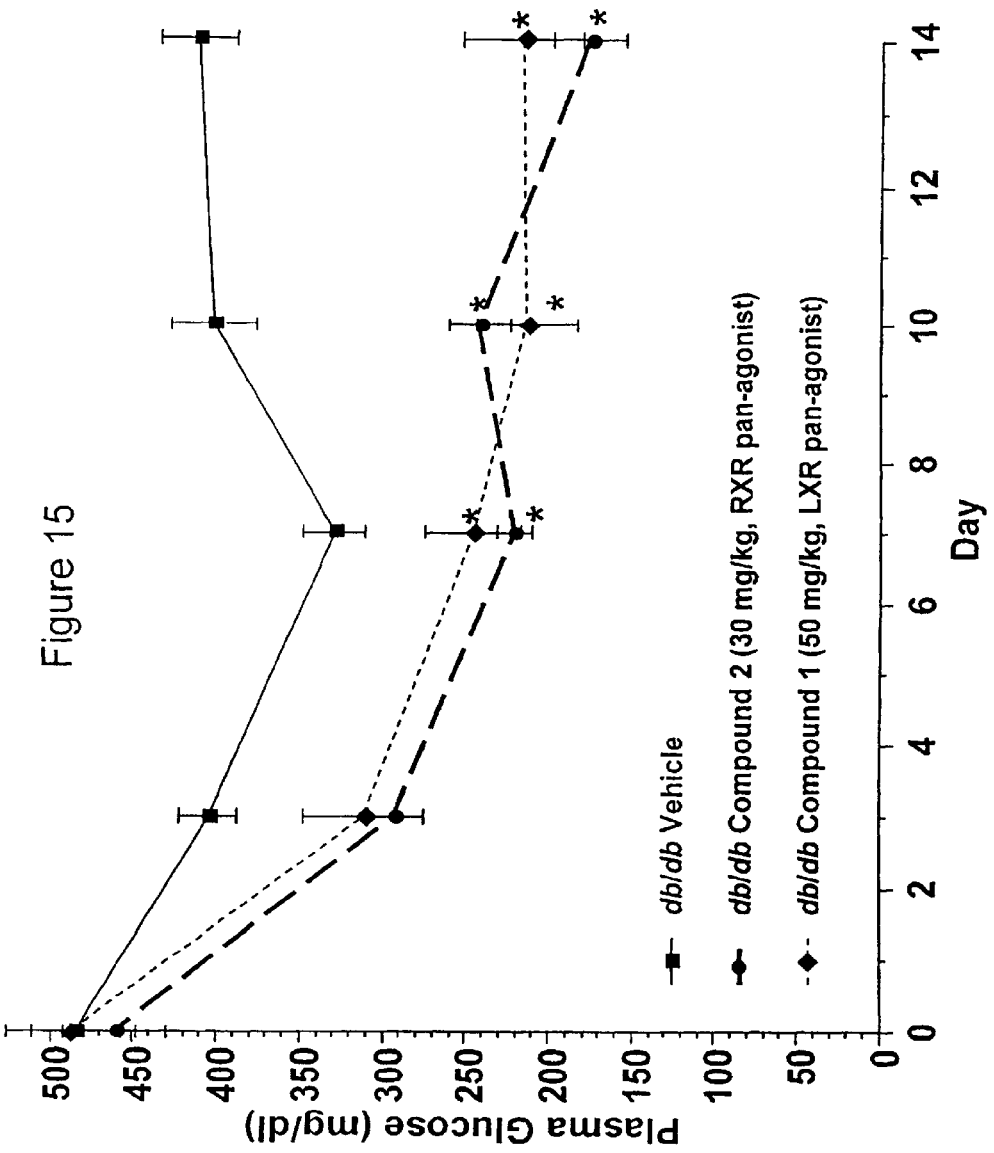

METHODS FOR AFFECTING VARIOUS DISEASES UTILIZING LXR COMPOUNDS

TECHNICAL FIELD

The present invention relates to LXRβ-selective agonists and their use in increasing reverse cholesterol transport, elevating the plasma level of high density lipoprotein (HDL) in a mammal, and in treating metabolic disorders including, but not restricted to, cardiovascular disease, diabetes, obesity, gallstone disease, syndrome X, hypertension, hypercholesterolemia, cholesterol absorption or transport disease, HDL deficiencies, and hyperlipidemia.

Also provided by the present invention are methods for decreasing hyperglycemia and insulin resistance, and methods for treating type II diabetes and reducing the cardiovascular complications of type II diabetes, said methods comprising administering to said mammal, a therapeutically-effective amount of an LXR agonist.

Further provided are methods for treating obesity, and methods for treating the complications of obesity including type II diabetes, cardiovascular disease, hyperlipidemia, and hypertension, said methods comprising administering a therapeutically-effective amount of an LXRα-selective antagonist. Also included in the present invention are methods of identifying said agonists and antagonists.

BACKGROUND OF THE INVENTION

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. There are five classifications of lipoproteins based on their degree of density: chylomicrons; very low density lipoproteins (VLDL); low density lipoproteins (LDL); intermediate density lipoproteins (IDL); and high density lipoproteins (HDL). Such classifications are commonly known to those of skill in the art and are described, for example, in the *Merck Manual*, 16th Ed. 1992 (see, for example, pp. 1039–1040) and "Structure and Metabolism of Plasma Lipoproteins" in *Metabolic Basis of Inherited Disease*, 6th Ed. 1989, pp. 1129–1138.

One form of hyperlipidemia is hypercholesterolemia, characterized by the existence of elevated LDL cholesterol levels. The initial treatment for hypercholesterolemia is often to modify the diet to one that is low in fat and cholesterol, coupled with appropriate physical exercise, followed by drug therapy when LDL-lowering goals are not met by diet and exercise alone. LDL is commonly known as the "bad" cholesterol, whereas HDL is the "good" cholesterol. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., *Am I. Med.*, 62:707–714 (1977); Stampfer, et al., *N. England J. Med.* 325:373–381 (1991); and Kannel, et al., *Ann. Internal Med.*, 90:85–91 (1979).

Members of the nuclear hormone receptor superfamily function as ligand-dependent transcription factors that regulate genetic networks controlling important biological processes such as cell growth, development, and metabolism. In particular members of the Liver X Receptor (LXR) subgroup regulate transcription of genes involved in the coordinate regulation of cholesterol and lipid metabolism. The LXR subfamily of nuclear receptors is comprised of two iso-types, LXRα and LXRβ, which are encoded by independent genes. The two iso-types exhibit approximately 80% identity throughout their DNA binding and ligand binding domains. LXRα is highly expressed in liver, intestine, fat, and kidney, and expressed at lower, but detectable, levels in the adrenal gland, muscle, and cells of the hematopoetic system. In contrast, LXRβ is ubiquitously expressed in all tissues and cell types examined. Nevertheless, both iso-types are coexpressed in cell types that are involved in cholesterol metabolism and homeostasis such as hepatocytes (liver), intestinal enterocytes, and macrophages.

Numerous studies have shown that increased levels of HDL are associated with lower risks for cardiovascular disease. In contrast, elevated levels of non-HDL cholesterol lead to increased risks for cardiovascular disease. LXRα and LXRβ regulate several genes involved in HDL metabolism including those encoding the apolipoprotein ApoE, which is an essential component of the HDL particle, and the ATP binding cassette transporters ABCA1 and ABCG1. ABCA1 and ABCG1 function as efflux pumps that mediate the transfer of intracellular cholesterol out of cells to HDL particles, a process referred to as reverse cholesterol transport. Importantly humans with mutations in the ABCA1 gene suffer from Tangier disease and exhibit decreased levels of reverse cholesterol transport, decreased levels of HDL, and increased rates of coronary heart disease. Tangier disease patients also exhibit massive accumulation of cholesterol in their macrophages. Cholesterol laden macrophages are major components of atherosclerotic plaques and these cells are thought to play a key role in plaque formation and progression to cardiovascular disease.

The ability to control the efflux of intracellular cellular cholesterol is also important in the intestine. Studies have demonstrated that increasing ABCA1 levels limits the absorption of dietary cholesterol by stimulating the efflux of absorbed cholesterol out of enterocytes and into the intestinal lumen where it is excreted. An additional site of LXR activity is the liver where LXRs are involved in the expression of the CYP7a, the gene encoding the enzyme cholesterol 7α-hydroxylase. Cholesterol 7α-hydroxylase is the rate-limiting enzyme in the metabolic conversion of cholesterol to bile acids.

Some studies demonstrate that LXR agonists also produce significant increases in the level of serum triglycerides. High levels of serum triglycerides are known to increase the risk of cardiovascular disease and other metabolic diseases. Thus triglyceride elevation significantly decreases the therapeutic index of certain LXR agonists for the treatment of cardiovascular disease.

In view of the foregoing, there remains a need in the art for compounds and methods that can be used to regulate LXRs and, in turn, to control the balance of cholesterol metabolism and fatty acid biosynthesis. More particularly, there remains a need in the art for compounds and methods that can be used to increase HDL levels and, thus, to treat disorders associated with bile acid and cholesterol metabolism. The present invention fulfills these and other needs.

SUMMARY OF THE INVENTION

It has now been discovered that ligands which are selective agonists of LXRβ are useful for increasing reverse cholesterol transport, increasing conversion of cholesterol to bile acids, decreasing low density lipoprotein (LDL) levels, decreasing absorption of dietary cholesterol, elevating high density lipoprotein (HDL) levels, and treating metabolic disorders. Preferably, the LXRβ selective agonist acts without substantially elevating the triglyceride plasma level. In one aspect, the present invention provides methods for elevating or raising, i.e., increasing, HDL plasma levels in a mammal in need of such treatment, the methods comprising administering to the mammal, e.g., a human, an HDL-elevating amount of a LXRβ selective agonist.

Any compound that activates and is a selective agonist of LXRβ can be used in the methods of the present invention. More particularly, any compound that is found to be a selective agonist of LXRβ using either in vitro or in vivo assay procedures, such as those described herein, can be used in the methods of the present invention, including those that are concomitantly an LXRβ agonist and an LXRα partial agonist or antagonist.

In another aspect, the present invention provides methods for preventing, halting or slowing the progression of metabolic diseases, such as atherosclerotic cardiovascular diseases and related conditions, in a mammal in need of such treatment, the methods comprising administering to the mammal a therapeutically-effective amount of a LXRβ selective agonist.

In yet another aspect, the present invention provides methods for elevating HDL plasma levels, preventing, halting or slowing the progression of metabolic conditions, such as atherosclerotic cardiovascular diseases and related conditions, in a mammal in need of such treatment, the methods comprising administering to the mammal a therapeutically-effective amount of a LXRβ selective agonist in combination with one or more additional active agents, such as bile acid sequestrants, nicotinic acid, fibric acid derivatives, ACAT inhibitors, and HMG CoA reductase inhibitors.

Also provided are methods of decreasing the absorption of cholesterol in the intestine of a mammal in need of such treatment, by administering to said mammal an LXRβ selective agonist and methods of regulating HDL-associated gene expression in a cell, by administering an LXRβ selective agonist. Typically, the gene is encoded by a protein or polypeptide selected from the group consisting of ABCA1, ABCG1, CYP7A, ApoE, lipoprotein lipase, and pro-inflammatory genes.

The present invention provides methods of decreasing the plasma level of LDL in a mammal, by administering an LXRβ selective agonist, wherein the plasma level of triglycerides is not elevated or is not substantially elevated.

Further provided are methods of identifying an LXRβ selective agonist comprising:

a) selecting a candidate compound;

b) testing the candidate compound in a cell-based or biochemical assay that measures the LXRα and LXRβ agonist activity of the compound; and c) identifying those candidate compounds which are LXRβ selective agonist as those compounds whose potency is lower for LXRβ as compared to LXRα; and/or whose efficacy is higher for LXRβ as compared to LXRα. or by a) selecting a candidate compound;

b) contacting the candidate compound with a cell expressing LXRβ only and a first reporter gene containing DNA sequences to which LXRβ binds; and also contacting the candidate compound with a cell expressing LXRα only and a second reporter gene containing DNA sequences to which LXRα binds;

c) determining if the candidate is an LXRβ agonist and/or an LXRα agonist by examining the ability of the compound to induce transcription of the reporter gene under control of LXRβ and LXRα; and d) identifying those candidate compounds which are LXRβ selective agonists as those compounds whose potency is lower for LXRβ as compared to LXRα; and/or whose efficacy is higher for LXRβ as compared to LXRα.

Further provided are methods for decreasing hyperglycemia and insulin resistance in a mammal, and associated cardiovascular complications arising from hyperglycemia and insulin resistance, said method comprising administering to said mammal in need of such treatment a therapeutically-effective amount of an LXR agonist; methods for treating type II diabetes in a mammal, said method comprising administering to said mammal in need of such treatment a therapeutically-effective amount of an LXR agonist; and methods for treating type II diabetes in a mammal and reducing the cardiovascular complications of type II diabetes, said method comprising administering to said mammal in need of such treatment a therapeutically-effective amount of an LXR agonist.

The invention also provides methods for treating obesity in a mammal, said method comprising administering to said mammal in need of such treatment a therapeutically-effective amount of an LXRα-selective antagonist; and methods for treating the complications of obesity in a mammal including type II diabetes, cardiovascular disease, hyperlipidemia, and hypertension, said method comprising administering to said mammal in need of such treatment a therapeutically-effective amount of an LXRα-selective antagonist.

Also included in this invention are methods of identifying an LXRα selective antagonist comprising:

a) selecting a candidate compound;

b) testing the candidate compound in a cell-based or biochemical assay that measures LXRα and LXRβ antagonist activity of the compound; and c) identifying those candidate compounds which are LXRα selective antagonists as those compounds whose potency is lower for LXRα as compared to LXRβ; and/or whose efficacy as an antagonist is higher for LXRα as compared to LXRβ; or by a) selecting a candidate compound;

b) contacting the candidate compound with a cell expressing LXRα only and a first reporter gene containing DNA sequences to which LXRα binds; and also contacting the candidate compound with a cell expressing LXRβ only and a second reporter gene containing DNA sequences to which LXRβ binds; and treating both sets of cells with LXR pan-agonist to induce transcription of the reporter gene;

c) determining if the candidate is an LXRα antagonist and/or an LXRβ antagonist by examining the ability of the compound to inhibit the pan-agonist induced transcription of the reporter gene under control of LXRα and LXRβ; and d) identifying those candidate compounds which are LXRα selective antagonists as those compounds whose potency is lower for LXRα as compared to LXRβ; and/or whose efficacy as an antagonist is higher for LXRα as compared to LXRβ.

BRIEF DESCRIPTION OF THE DRAWINGS

FIG. 15 illustrates the effect of the LXR pan-agonist Compound 1 on plasma glucose levels in db/db mice. Compound 1 (50 mg/kg) was dosed daily for seven days by oral gavage. Glucose levels were determined from plasma samples taken on days 0 (one day prior to the first dose), 1, 3, and 7. Data presented is the average value derived from eight animals in each group. *Signifies the value is statistically different from the vehicle control value.

DETAILED DESCRIPTION

Figure 1:
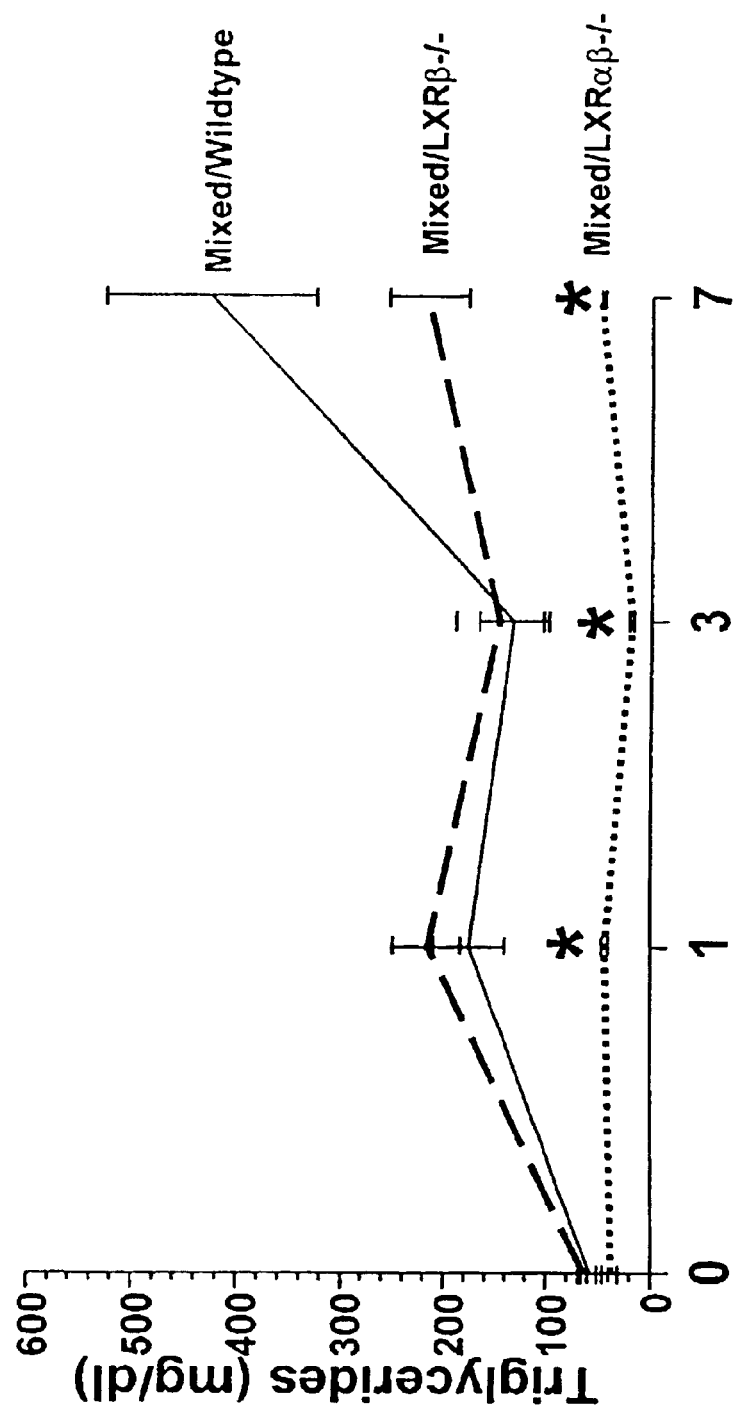
FIG. 1 illustrates the effect of the LXR pan-agonist Compound 1 on triglyceride levels in mixed wildtype (C57BL/6xA129), LXRβ−/−, and LXRαβ−/− mice. Compound 1(10 mg/kg) was dosed daily for seven days by oral gavage. Triglyceride levels were determined from plasma samples taken on days 0 (one day prior to the first dose), 1, 3, and 7. Data presented is the average value derived from seven animals in each group except for LXRα$^{-/-}$-C57BL/6 which is the average of six animals. *Signifies that the value is statistically different from the wildtype control value.

The present invention provides methods for preventing or reducing the risk of developing a metabolic disease, such as, atherosclerosis, the methods comprising the administration of a prophylactically effective amount or, more particularly, an HDL-raising amount of a LXRβ selective agonist, either alone or in combination with one or more additional pharmaceutically active agents, to a mammal, particularly a human, who is at risk of developing the metabolic disease.

LXRβ selective agonists also can be used in methods for treating, halting or slowing the progression of a metabolic disease, such as atherosclerotic disease, once it has become clinically evident, the methods comprising the administration of a therapeutically effective amount or, more particularly, an HDL-raising amount of a LXRβ agonist, either alone or in combination with one or more additional pharmaceutically active agents, to a mammal, particularly a human, who already has the metabolic or atherosclerotic disease.

Atherosclerosis encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease including multi-infarct dementia, and peripheral vessel disease including erectile dysfunction, are all clinical manifestations of atherosclerosis and are, therefore, encompassed by the terms "atherosclerosis" and "atherosclerotic disease."

The present invention further provides methods for preventing or reducing the risk of a first or subsequent (where the potential exists for recurrence) metabolic disease event, the methods comprising the administration of a prophylactically effective amount or, more particularly, an HDL-raising amount of a LXRβ selective agonist, either alone or in combination with one or more additional pharmaceutically active agents, to a mammal, particularly a human, who is at risk for having a metabolic or an atherosclerotic disease event. The term "atherosclerotic disease event" as used herein, is intended to encompass coronary heart disease events, cerebrovascular events, and intermittent claudication. Coronary heart disease (CHD) events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. It is intended that persons who have previously experienced one or more non-fatal atherosclerotic disease event are those for whom the potential for recurrence of such an event exists. The invention also serves to remove cholesterol from tissue deposits such as atherosclerotic plaques or xanthomas in a patient with atherosclerotic disease manifest by clinical signs, such as angina, claudication, bruits, one that has suffered a myocardial infarction or transient ischemic attack, or one diagnosed by angiography, sonography or MRI.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include, but are not limited to, hypertension, smoking, diabetes, low levels of high density lipoprotein cholesterol, high levels of low density lipoprotein cholesterol, and a family history of atherosclerotic cardiovascular disease. Published guidelines for determining those who are at risk of developing atherosclerotic disease can be found in: Third Report of the National Cholesterol Education Program, Expert Panel on *Detection, Evaluation, and Treatment of high Blood Cholesterol in Adults* (*Adult Treatment Panel III*), National Institutes of Health, National Heart Lung and Blood Institute, NIH Publication No. 01-3670, May 2001. People identified as having one or more of the above-noted risk factors, as well as people who already have atherosclerosis, are intended to be included within the group of people considered to be at risk for having an atherosclerotic disease event.

As explained above, the present invention provides methods of raising, i.e., increasing, the plasma level of high density lipoprotein (HDL) in a mammal, the methods comprising administering to the mammal an HDL-raising amount of an LXRβ selective agonist. As such, any compound that activates and is a selective agonist of LXRβ can be used in the methods of the present invention. More particularly, any compound that is found to be a selective agonist of LXRβ using in vitro or in vivo assay procedures, such as those described herein, can be used in the methods of the present invention.

The present invention also provides a method for increasing reverse cholesterol transport utilizing an LXRβ selective agonist. Reverse cholesterol transport clears cholesterol from the plasma or serum. Therefore, an increase in clearance has a beneficial effect upon the patient even in the event that HDL is also rapidly cleared.

Also provided by the present invention is a method for decreasing the absorption of dietary cholesterol or decreasing the LDL plasma level in a mammal, such as by increasing the conversion of cholesterol to bile acids. Again, a patient benefits from these methods, since the overall cholesterol levels of LDL and other forms of cholesterol are reduced.

"LXRβ selective agonist" includes a partial agonist or agonist that exhibits about a two to about a ten-fold preference for LXRβ compared to LXRα in potency ($EC_{50}$, the concentration that achieves about 50% of the agonist's maximum transcriptional activity) and/or efficacy (the maximum transcriptional activity searched relative to a known control set at 100%). To be LXRβ selective, the agonist must activate LXRβ at a lower concentration than the concentration needed to activate LXRα. In addition the selective agonist can interact with both receptors with similar affinity but promotes selective activation of transcription by LXRβ. Preferably, a LXRβ selective agonist favors LXRβ in both potency and efficacy at about a two to about a five-fold preference.

"Reporter gene" means any gene that encodes a product whose expression is detectable and/or quantifiable by physical, immunological, chemical, biochemical, or biological assays. A reporter gene product may, for example, have one of the following attributes, without restrictions: a specific nucleic acid chip hybridization pattern, fluorescence (e.g., green fluorescent protein), enzymatic activity, toxicity, or an ability to be specifically bound by a second molecule, labeled or unlabeled. Preferably the same reporter gene is used for LXRβ and LXRα, however, reporter genes specific to one or the other receptor can be used. More preferably, firefly luciferase is used. A number of reporter genes can be used so long as they are placed under the transcriptional control of LXRβ and/or LXRα with the proper DNA sequences.

"LXR" means nuclear receptors LXRα and LXRβ and all subtypes, as well as the corresponding genes. LXRβ includes human LXRβ (GenBank Accession Number P55055; Apfel, et al. *Mol. Cell. Biol.* 14:7025–7035 (1994); Willy, et al. *Genes Dev.* 9:1033–1045 (1995); and Long, et al. *Proc. Nat'l. Acad. Sci., USA* 91:10809–10813 (1995).) LXRβ includes LXRb, LXR beta, NER, NER1, UR, OR-1, R1P15, NR1H2 or any homologue.

"Metabolic diseases" are those resulting from disorders of cholesterol, lipid, and/or glucose metabolism, including, but not limited to, cardiovascular disease, such as atherosclerosis, diabetes, obesity, syndrome X, hypertension, hypercholesterolemia, hyperlipidemia, HDL deficiencies, cholesterol absorption or transport disorders, and gallstone diseases. (Syndrome X includes the combination of insulin resistance, hypertension, hyperlipidemia, type II diabetes, and obesity commonly seen in a number of patients.)

Method of identifying the LXRβ selective agonists include:

a) selecting a candidate compound;

b) testing the candidate compound in a cell-based or biochemical assay that measures the LXRα and LXRβ agonist activity of the compound; and c) identifying those candidate compounds which are LXRβ selective agonist as those compounds whose potency is lower for LXRβ as compared to LXRα; and/or whose efficacy is higher for LXRβ as compared to LXRα; or by a) selecting a candidate compound;

b) contacting the candidate compound with a cell expressing LXRβ only and a first reporter gene containing DNA sequences to which LXRβ binds; and also contacting the candidate compound with a cell expressing LXRα only and a second reporter gene containing DNA sequences to which LXRα binds;

c) determining if the candidate is an LXRβ agonist and/or LXRα agonist by examining the ability of the compound to induce transcription of the reporter gene under control of LXRβ and LXRα; and d) identifying those candidate compounds which are LXRβ selective agonists as those compounds whose potency is lower for LXRβ as compared to LXRα; and/or whose efficacy is higher for LXRβ as compared to LXRα.

The following is an exemplar strategy that can be used for the identification and screening of LXRβ agonists that are useful as cholesterol-lowering agents. First, a high throughput screen (HTS) is used to identify compounds that bind to LXRβ. Compounds that exhibit binding are next tested for ability to enhance LXRβ-mediated transactivation and for specificity of binding to the LXRβ. Those LXRβ compounds that exhibit favorable activity are then tested for cytotoxicity. Compounds that are nontoxic at the range of expected clinical dosage are then tested for pharmacokinetic (PK) and structure-activity relationship (SAR) activity. Finally, the lead compounds having the most favorable properties are tested in animal studies, including studies in hypercholesterolemic and metabolic disease model systems.

More particularly, compounds can be evaluated in vitro for their ability to activate LXR receptor function using biochemical assays or in cell-based assays, such as that described in Lehmann. et al., *J. Biol Chem.*, 272(6) 3137–3140 (1997). Alternatively, the compounds and compositions can be evaluated for their ability to increase or decrease gene expression modulated by LXR, using Northern-blot analysis to measure RNA levels or Western-blot analysis to measure expression of proteins encoded by LXR target genes. Established animal models to evaluate hypercholesterolemic effects of the compounds are also known in the art. For example, compounds disclosed herein can lower cholesterol levels in hamsters fed a high-cholesterol diet, using a protocol similar to that described in Spady, et al., *J Clin. Invest.*, 81:300 (1988); Evans, et al., *J. Lipid Res.*, 35:1634 (1994), and Lin, et al., *J. Med. Chem.*, 38:277 (1995). Still further, LXR animal models (e.g., LXR knockout mice) can be used for evaluation of the present compounds and compositions (see, for example, Peet, et al., *Cell*, 93:693–704 (1998)).

Using the foregoing assays, numerous compounds can be screened for their ability to modulate, i.e., activate, LXRβ. Essentially any chemical compound can be screened as a potential modulator of LXRs, although most often compounds that can be dissolved in aqueous solutions are used. In preferred embodiments, the assays are designed to screen large chemical libraries by automating the assay steps and providing compounds from any convenient source to assay, which are typically about 10 μM in parallel (e.g., in microliter formats on microliter plates in robotic assays). It will be appreciated by those of skill in the art that there are many commercial suppliers of chemical compounds, including Sigma Chemical Co. (St. Louis, Mo.), Aldrich Chemical Co. (St. Louis, Mo.), Sigma-Aldrich (St. Louis, Mo.), Fluka Chemika-Biochemica Analytika (Buchs, Switzerland), and the like.

In one preferred embodiment, high throughput screening methods involve providing a combinatorial library containing a large number of potential therapeutic compounds (i.e., LXR agonists). Such "combinatorial chemical libraries" are then screened in one or more assays, as described herein, to identify those library members (particular chemical species or subclasses) that display a desired characteristic activity, i.e., activate LXRs. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in every possible way for a given compound length (i e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.*, 37:487–493 (1991) and Houghton, et al., *Nature,* 354:84–88 (1991)). Other chemistries for generating chemical diversity libraries can also be used. Such chemistries include, but are not limited to, peptides (PCT Publication No. WO 91/19735); encoded peptides (PCT Publication WO 93/20242); random biooligomers (PCT Publication No. WO 92/00091); benzodiazepines (U.S. Pat. No. 5,288,514); diversomers, such as hydantoins, benzodiazepines and dipeptides (Hobbs, et al, *Proc. Nat. Acad. Sci. USA,* 90:6909–6913 (1993)); vinylogous polypeptides (Hagihara, et al., *J. Amer. Chem. Soc.* 114:6568 (1992)); nonpeptidal peptidomimetics with $\beta$-D-glucose scaffolding (Hirschmann, et al., *J. Amer. Chem. Soc.,* 114:9217–9218 (1992)); analogous organic syntheses of small compound libraries (Chen, et al, *J. Amer. Chem. Soc.,* 116:2661 (1994)); oligocarbamates (Cho, et al., *Science,* 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309–314 (1996) and PCT/US96/10287); carbohydrate libraries (see, e.g., Liang, et al., *Science,* 274:1520–1522 (1996) and U.S. Pat. No. 5,593,853); small organic molecule libraries (see, e.g., benzodiazepines, Baum C&E News, Jan. 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Russia, Tripos, Inc., St. Louis, Mo., ChemStar, Ltd., Moscow, Russia, 3D Pharmaceuticals, Exton, Pa., Martek Biosciences, Columbia, Md.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Russia, Tripos, Inc., St. Louis, Mo., ChemStar, Ltd., Moscow, Russia, 3D Pharmaceuticals, Exton, Pa., Martek Biosciences, Columbia, N. Mex.).

Using the in vitro assays disclosed herein, compounds can be readily screened for their ability to activate LXRs in a high-throughput format. In such high throughput assays, it is possible to screen up to several thousand different potential LXR$\beta$ selective agonists in a single day. In particular, each well of a microliter plate can be used to run a separate assay against a selected potential LXR modulator, or if concentration or incubation time effects are to be observed, every 5–10 wells can test a single LXR modulator. Thus, a single standard microliter plate can assay about 100 (96) modulators. If 1536 well plates are used, then a single plate can easily assay from about 100–about 1500 different compounds. It is possible to assay many different plates per day; assay screens for up to about 6,000–20,000, and even up to about 100,000–1,000,000 different compounds is possible using the integrated systems of the invention.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.). These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

The compounds, i.e., the LXR$\beta$ selective agonists, of this invention can be incorporated into a variety of formulations for therapeutic administration. More particularly, the compounds of the present invention can be formulated into pharmaceutical compositions by combination with appropriate, pharmaceutically acceptable carriers or diluents. Suitable formulations for use in the present invention are found in *Remington's Pharmaceutical Sciences* (Mack Publishing Company, Philadelphia, Pa., 17th ed. (1985)). In addition, for a brief review of methods for drug delivery (see, Langer, *Science,* 249:1527–1533 (1990)).

As used herein, the term "composition" is intended to encompass a product comprising the specified ingredients (e.g., LXR$\beta$ selective agonist), as well as any product that results directly or indirectly from combination of the specified ingredients.

The active LXR$\beta$ selective agonist compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampoules, sachets, elixirs, suspensions, syrups, and the like. The active compounds can also be administered intranasally as, for example, liquid drops or spray. Oral administration is preferred. Such compositions and preparations should contain at least 0.1 percent of active compound, i.e. the LXR$\beta$ selective agonist. The preferred percentage of active compound in these compositions may, of course, be varied and may conveniently be between about 2% to about 60% of the weight of the unit.

Therapeutically effective amounts, prophylactically effective amounts and/or high density lipoprotein-raising, amounts of the LXR agonist are suitable for use in the compositions and methods of the present invention. The term "therapeutically effective amount" is intended to mean that amount of a drug or pharmaceutical agent that will elicit the biological or medical response of a tissue, a system, animal or human that is being sought by a clinician, such as a researcher, veterinarian, medical doctor or osteopathic doctor.

The term "prophylactically effective amount" is intended to mean that amount of a drug or pharmaceutical agent that will prevent or reduce the risk of occurrence of a metabolic disease condition, such as atherosclerosis or an atherosclerotic disease event.

The term "high density lipoprotein-raising or elevating amount" is intended to mean an amount of a drug or pharmaceutical agent that will elevate a subject's plasma HDL level above the level it was at prior to administration of the drug or pharmaceutical agent. Measurement of plasma HDL levels can be performed using any medically acceptable procedures known to those skilled in the medical arts.

The dosage regimen utilizing a LXR agonist is selected in accordance with a variety of factors including type, species, age, weight, sex and medical condition of the patient; the severity of the condition to be treated; the route of administration; the renal and hepatic function of the patient; and the particular LXR agonist or derivative thereof employed. A consideration of these factors is well within the purview of the ordinarily skilled clinician for the purpose of determining an appropriate HDL-raising amount of the LXR agonist, as well as the therapeutically effective amounts of the LXR agonist needed to prevent, counter, or arrest the progress of the condition.

For example, the compounds of the present invention can be administered at a daily dosage of from about 0.01 milligram to about 100 milligram per kilogram of animal body weight, once a day or given in divided doses two to six times a day, or in sustained release form. For most large mammals, the total daily dosage is from about 1.0 milligram to about 1000 milligrams, and preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds, i.e., the LXR agonists, may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In the above-described methods, the LXR agonist may be administered either alone or in combination with one or more additional active agents. Combination therapy includes administration of a single pharmaceutical dosage formulation which contains a LXR agonist and one or more additional active agents, as well as administration of the LXR agonist and each active agent in its own separate pharmaceutical dosage formulation. For example, a LXR agonist and an HMG-CoA reductase inhibitor can be administered to the patient together in a single oral dosage composition such as a tablet or capsule, or each agent administered in separate oral dosage formulations. Where separate dosage formulations are used, the LXR agonist and one or more additional active agents can be administered at essentially the same time, i.e., concurrently, or at separately staggered times, i.e., sequentially; combination therapy is understood to include all these regimens.

For example, the LXR agonist may be administered in combination with one or more of the following active agents: an antihyperlipidemic agent; a plasma HDL-raising agent; an antihypercholesterolemic agent, such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor, such as melinamide; probucol; nicotinic acid and the salts thereof and niacinamide; a cholesterol absorption inhibitor such as beta-sitosterol; a bile acid sequestrant anion exchange resin, such as cholestyramine, colestipol or a dialkylaminoalkyl derivatives of a cross-linked dextrin; an LDL (low density lipoprotein) receptor inducer; fibrates such as clofibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); anti-oxidant vitamins, such as vitamin C and E, and beta carotene: a betablocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the LXR agonist can be administered in combination with more than one additional active agent, for example, a combination of LXR agonist with an HMG-CoA reductase inhibitor and aspirin, or LXR agonist, with an HMG-CoA reductase inhibitor and a beta blocker.

The LXR agonist is preferably administered with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulas of these and additional HMG-CoA reductase inhibitors that can be used in the methods of the present invention are described at page 87 of M. Yalpani, "Cholesterol Lowering Drugs," Chemistry & Industry, pp. 85–89 (5 Feb. 1996). In presently preferred embodiments, the HMG-CoA reductase inhibitor is selected from lovastatin and simvastatin.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the HMG-CoA reductase inhibitor is preferred.

LXR α and/or β agonists can be utilized in methods for decreasing hyperglycemia and insulin resistance or for methods of treating type II diabetes. The agonists can be identified, formulated, and administered as described above for the LXRβ selective agonists.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927) 5: 1061–1079). Epidemiological studies since then have confirmed the association and have shown a several-fold increase in coronary deaths among diabetic subjects when compared with nondiabetic subjects (see, e.g., Garcia, M. J. et al., Diabetes (1974) 23: 105–11 (1974); and Laakso, M. and Lehto, S., Diabetes Reviews (1997) 5(4): 294–315). Several lipoprotein abnormalities have been described among diabetic subjects (Howard B., et al., Arteriosclerosis (1978) 30: 153–162).

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., J. Basic & Clin. Phys. & Pharm. (1998) 9: 387–406 and Flier, J. Ann Rev. Med. (1983) 34:145–60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plasminogen activator inhibitor-1), has been referred to as "Syndrome X" (see, e.g., Reaven, G. M., Physiol. Rev. (1995) 75: 473–486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Type 2 diabetes often occurs in the face of normal, or even elevated, levels of insulin and can result from the inability of tissues to respond appropriately to insulin. Most type 2 diabetic patients are insulin resistant and have a relative deficiency of insulin, in that insulin secretion can not compensate for the resistance of peripheral tissues to respond to insulin. In addition, many type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of type 1 or type 2 diabetes.

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206–242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "treating" means the management and care of a human subject for the purpose of combating the disease, condition, or disorder and includes the administration of a compound of the present invention to prevent the onset of the symptoms or complications, alleviating the symptoms or complications, or eliminating the disease, condition, or disorder.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

The term "dyslipidemia" refers to abnormal levels of lipoproteins in blood plasma including both depressed and/or elevated levels of lipoproteins (e.g., elevated levels of LDL, VLDL and depressed levels of HDL).

Exemplary Primary Hyperlipidemia include, but are not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various beta. blockers; (3) dietary risk factors include dietary fat intake per total calories greater than 40%; saturated fat intake per total calories greater than 10%; cholesterol intake greater than 300 mg per day; habitual and excessive alcohol use; and obesity; and (4) non-genetic dyslipidemias.

The methods of the present invention can be used effectively in combination with one or more additional active diabetes agents depending on the desired target therapy (see, e.g., Turner, N. et al. Prog. Drug Res. (1998) 51: 33–94; Haffner, S. Diabetes Care (1998) 21: 160–178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999) 84: 1165–71; United Kingdom Prospective Diabetes Study Group: UKPDS 28, Diabetes Care (1998) 21: 87–92; Bardin, C. W.,(ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994) 121: 928–935; Coniff, R. et al., Clin. Ther. (1997) 19: 16–26; Coniff, R. et al., Am. J. Med. (1995) 98: 443–451; and Iwamoto, Y. et al, Diabet. Med. (1996) 13 365–370; Kwiterovich, P. Am. J. Cardiol (1998) 82(12A): 3U–17U). These studies indicate that diabetes and hyperlipidemia modulation can be further improved by the addition of a second agent to the therapeutic regimen.

An example of combination therapy that modulates (prevents the onset of the symptoms or complications associated) atherosclerosis, is administered with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrozol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin.

Still another example of combination therapy can be seen in modulating diabetes (or treating diabetes and its related symptoms, complications, and disorders) with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone);and related insulin sensitizers, such as selective and non-selective activators of PPARα, PPARΔ, and PPARγ; dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

Further provided by this invention are methods for treating obesity, as well as treating the complications of obesity, by administering an LXRα selective antagonist. The antagonists can be identified, formulated, and administered similarly to the information described above for the LXRβ selective agonist. A LXRα selective antagonist includes a partial agonist/antagonist or antagonist that exhibits about a two to about a ten-fold preference for LXRα compared to LXRβ in potency ($IC_{50}$, the concentration of compound that achieves 50% of the maximum reduction in the transcription activity achieved by the compound of interest observed in the presence of a sub-maximal concentration of LXR agonist) and/or efficacy (the maximum percent inhibition of transcription observed with the compound in question). To be LXRα selective, the antagonist must inhibit LXRα transcriptional at a low concentration than the concentration needed to inhibit LBRβ. In addition, the selective antagonist can interact with both receptors with similar affinity but promote selective inhibition of LXRα. Preferably, a LXRα selective antagonist favors LXRα in both potency and efficacy at about a two to about five-fold preference.

The terms "obese" and "obesity" refers to, according to the World Health Organization, a Body Mass Index (BMI) greater than 27.8 kg/$m^2$ for men and 27.3 kg/$m^2$ for women (BMI equals weight (kg)/height ($m^2$). Obesity is linked to a variety of medical conditions including diabetes and hyperlipidemia. Obesity is also a known risk factor for the development of type 2 diabetes (See, e.g., Barrett-Conner, E., Epidemol. Rev. (1989) 11: 172–181; and Knowler, et al., Am. J Clin. Nutr. (1991) 53:1543–1551).

Another example of combination therapy can be seen in treating obesity or obesity-related disorders, wherein the methods can be effectively used in combination with, for example, phenylpropanolamine, phentermine, diethylpropion, mazindol; fenfluramine, dexfenfluramine, phentiramine, $β_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

The following examples are intended to illustrate, but not to limit, the invention.

EXAMPLES

To decipher the physiological roles of LXRα and LXRβ mice, seven different lines of mice encompassing four unique LXR genotypes (LXRα+/+, LXRβ+/+=wildtype; LXRα-/-, LXRβ+/+=LXRα-/-; LXRα+/+, LXRβ-/-= LXRβ-/-; LXRα-/-, LXRβ-/-=LXRαβ-/-) were studied. Genetic knockouts of LXRα( LXRα-/-) were generated in two independent mouse strain backgrounds (C57BL/6 and A129). Genetic knockouts of LXRβ (LXRβ-/-) and the double knockout of LXRα and LXRβ (LXRαβ-/-) were generated in a mixed genetic background (C57BL/6×A129). The three appropriate wildtype (LXRα+/+, LXRβ+/+) mouse lines were used as controls. Mice from each line were treated for seven days with 10 mg compound/kg body weight of the LXR agonist Compound 1: N-(2,2,2-trifluoroethyl)-N-[4-(2,2,2- trifluoro-1-hydroxy-1-trifluoromethylethyl)-phenyl]-benzene sulfonamide. Compound 1 is considered a pan-LXR agonist that binds and activates both LXRα and LXRβ with similar potency and efficacy. Compound 1 was administered by daily oral gavage in a sesame oil/ethanol vehicle via a 1-cc syringe fitted with a 20G disposable feeding needle. Compound was solvated in ethanol (5% final volume) and brought up to final volume with sesame oil (Sigma, St. Louis, Mo.).

To determine the ability of Compound 1 to elevate serum triglycerides non-fasting mice were anesthetized with isofluorane and blood samples were obtained by retro-orbital plexus puncture. Blood samples were collected before the first dose and three hours after dosing on day 1, day 3 and day 7 into heparinized tubes. Samples were centrifuged to obtain plasma and stored at -20° C. Plasma triglyceride levels were determined using a colorimetric enzymatic assay adapted to a 96 well plate format (Infinity Triglyceride Reagent, Sigma, St. Louis, Mo.). Sigma glycerol standards (Sigma, St. Louis, Mo.) were use to generate standard curves. The absorbance of the samples and standards were read using a Multiskan plate reader. The results of this analysis (FIG. 1 and FIG. 2) demonstrate that the LXR pan-agonist elevates serum triglyceride levels only in mice that have LXRα (wildtype and LXRβ-/-). In contrast elimination of LXRβ (LXRβ-/-) has no effect on the ability of LXR agonists to elevate triglycerides. The analysis of triglyceride levels in LXR pan-agonist treated animals indicates that ability of LXR agonists to raise serum triglyceride levels is dependent upon LXRα.

Figure 3:
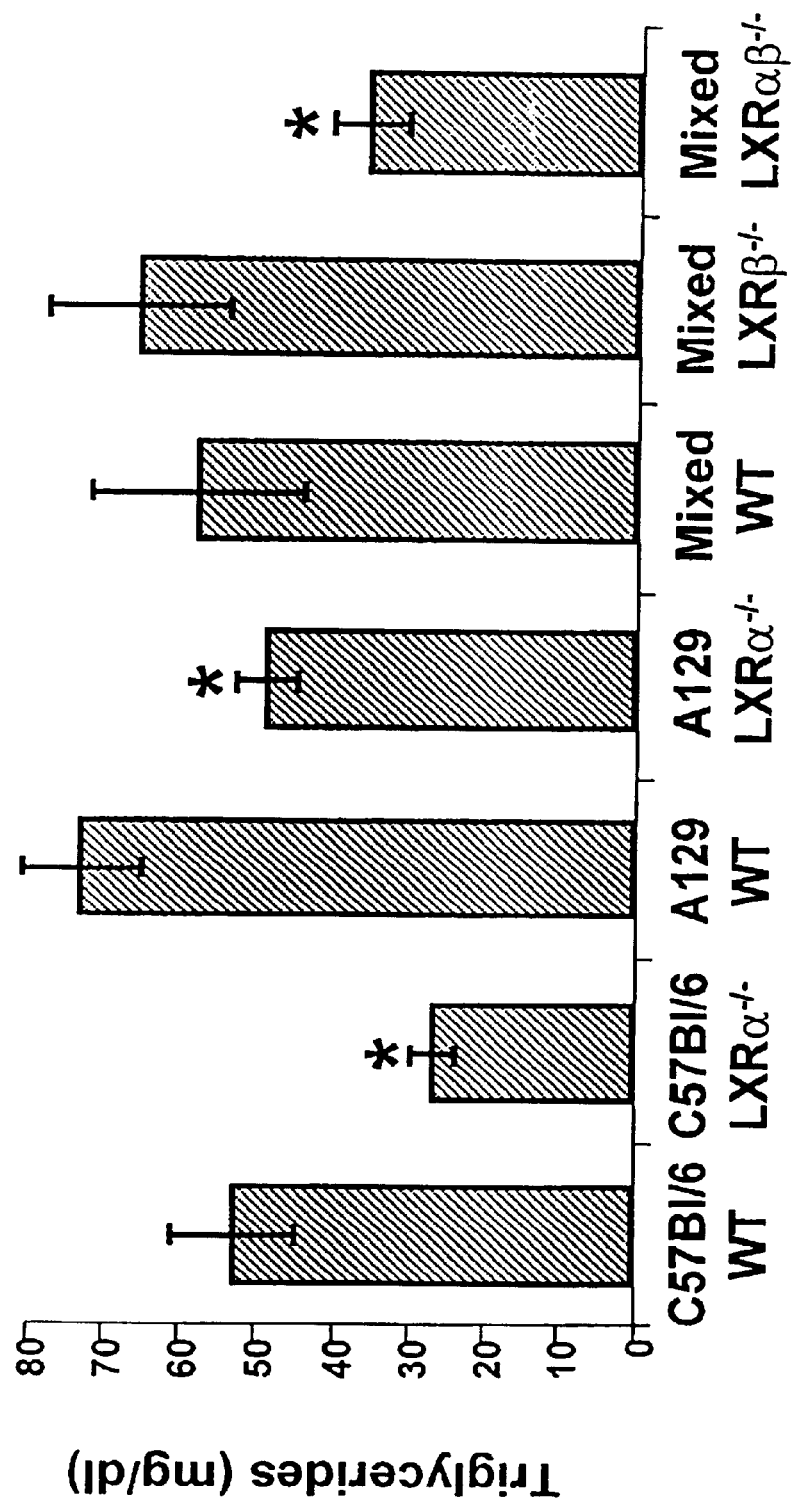
FIG. 3 illustrates the plasma triglyceride levels in untreated wildtype, LXRα-/-, LXRβ-/-, and LXRαβ-/- mice. Data presented is the average value derived from seven animals in each group except for LXRα$^{-/-}$/C57BL/6 which is the average of six animals. *Signifies that the value is statistically different from the wildtype control value.

Serum triglyceride levels were also measured as described above in animals on day 0 prior to the initial dose in order to determine the ability of LXRα and LXRβ to regulate triglyceride levels in the absence of pharmacological intervention. The data in FIG. 3 show that in the absence of LXRα (LXRα-/- and LXRβ-/-) triglyceride levels are significantly decreased relative to wildtype controls. Once again elimination of LXRβ (LXRβ-/-) has no effect. These results identify LXRα as the LXR iso-type responsible for regulating triglyceride levels.

Figure 4:
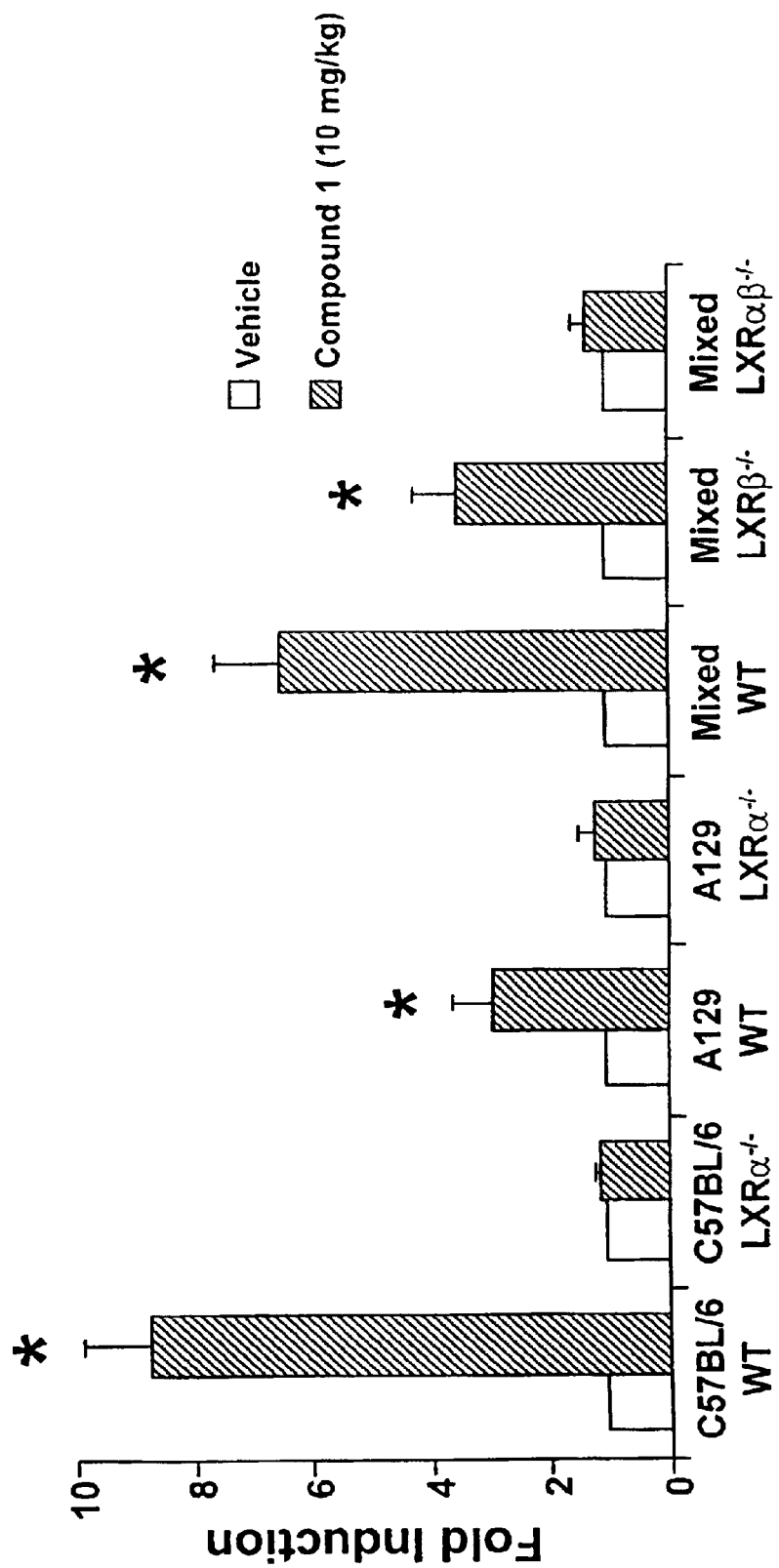
FIG. 4 illustrates the effect of the LXR pan-agonist Compound 1 on lipoprotein lipase (LPL) mRNA levels in wildtype, LXRα-/-, LXRβ-/-, and LXRαβ-/- mice. Compound 1 (10 mg/kg) was dosed daily for seven days by oral gavage. LPL levels were measured by quantitative PCR of total liver RNA. Data is expressed as fold induction by Compound 1 (+Compound 1/Vehicle, hatched bars). The value for vehicle treated mice in each group was set at 1.0 (white bars). Data is the average of four animals per group assayed in triplicate. *Signifies that the value is statistically different from the vehicle treated value within each genotype.

To further support the exclusive function of LXRα in triglyceride regulation, the ability of Compound 1 treatment to induce the mRNA encoding lipoprotein lipase (LPL) in the livers of treated animals was determined. Lipoprotein lipase is an enzyme that plays an essential role in triglyceride metabolism by promoting the transfer of triglycerides from lipoprotein particles to cells. To measure LPL mRNA levels, three hours after the final dose (day 7) animals were sacrificed, livers were harvested, and total liver RNA was isolated using RNeasy kits (QIAGEN Inc.) according to the supplier's total RNA isolation procedure. The RNA samples were further treated with deoxyribonuclease I to eliminate contaminating genomic DNA. LPL mRNA levels were than analyzed by real-time based quantitative PCR using Perkin Elmer ABI Prism 7700 and Sequence Detection System software (Perkin Elmer). FIG. 4 demonstrates that treatment of wildtype mice with the LXR pan-agonist increases the LPL mRNA from 3 to 9 fold calculated as fold induction by pan-agonist treatment (+Compound 1 /vehicle). Elimination of LXRα (LXRα-/-) completely blocks the pan-agonist induction of LPL in both the C57BL/6 and A129 mouse strain backgrounds. Elimination of LXRβ has little or no effect. Thus, as observed with triglyceride measurements, analysis of gene expression identifies LXRα as the LXR isotype responsible for regulating triglyceride levels. Taken together the results of these studies predict that an LXRβ-selective agonist will not elevate triglycerides.

Figure 2:
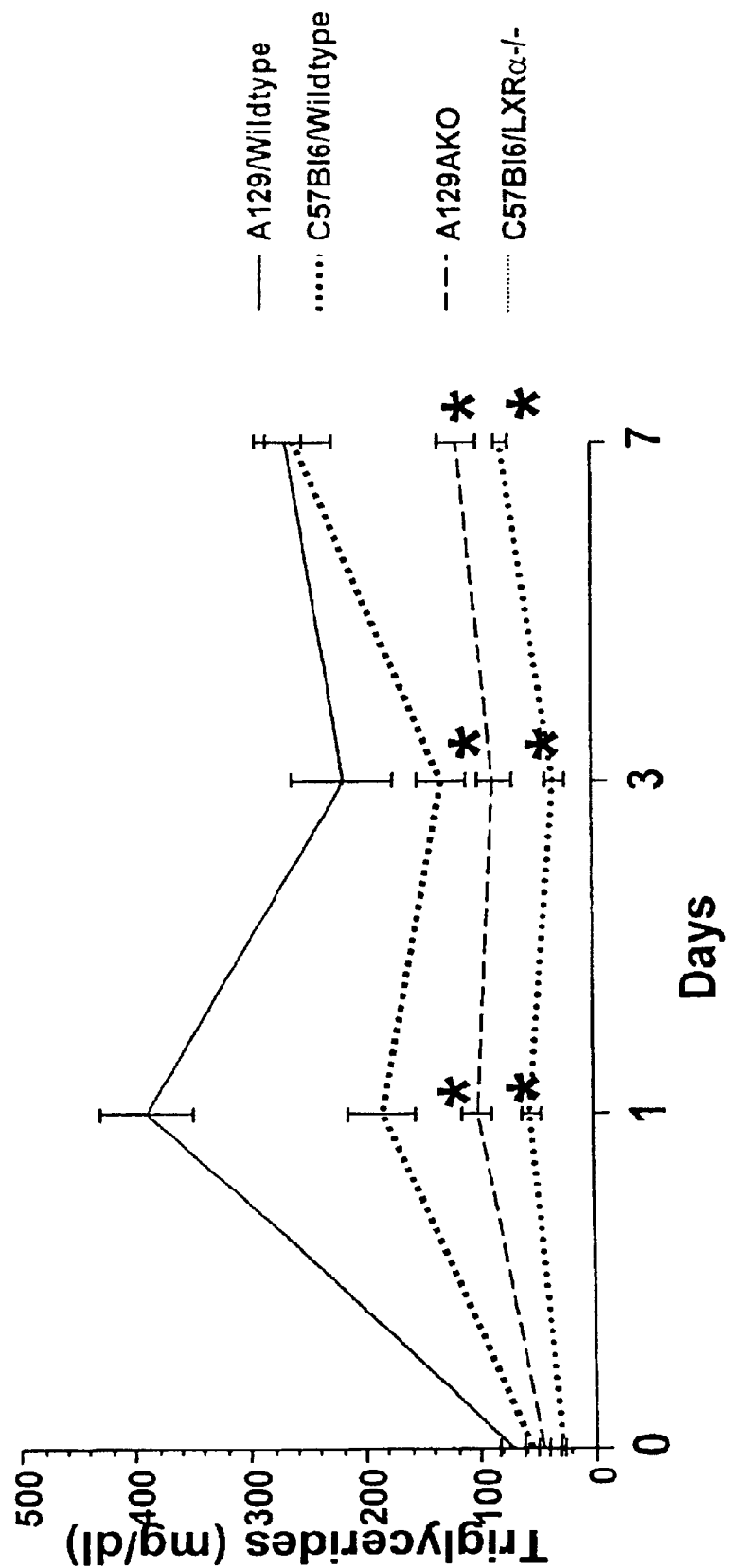
FIG. 2 illustrates the effect of the LXR pan-agonist Compound 1 on triglyceride levels in two strains of LXRα-/- mice (C57BL/6 and A129) and the appropriate wildtype controls. Compound 1 (10 mg/kg) was dosed daily for seven days by oral gavage. Triglyceride levels were determined from plasma samples taken on days 0 (one day prior to the first dose), 1, 3, and 7. Data presented is the average value derived from seven animals in each group except for LXRα$^{-/-}$/C57BL/6 which is the average of six animals. *Signifies that the value is statistically different from the appropriate strain-matched wildtype control value.
Figure 5:
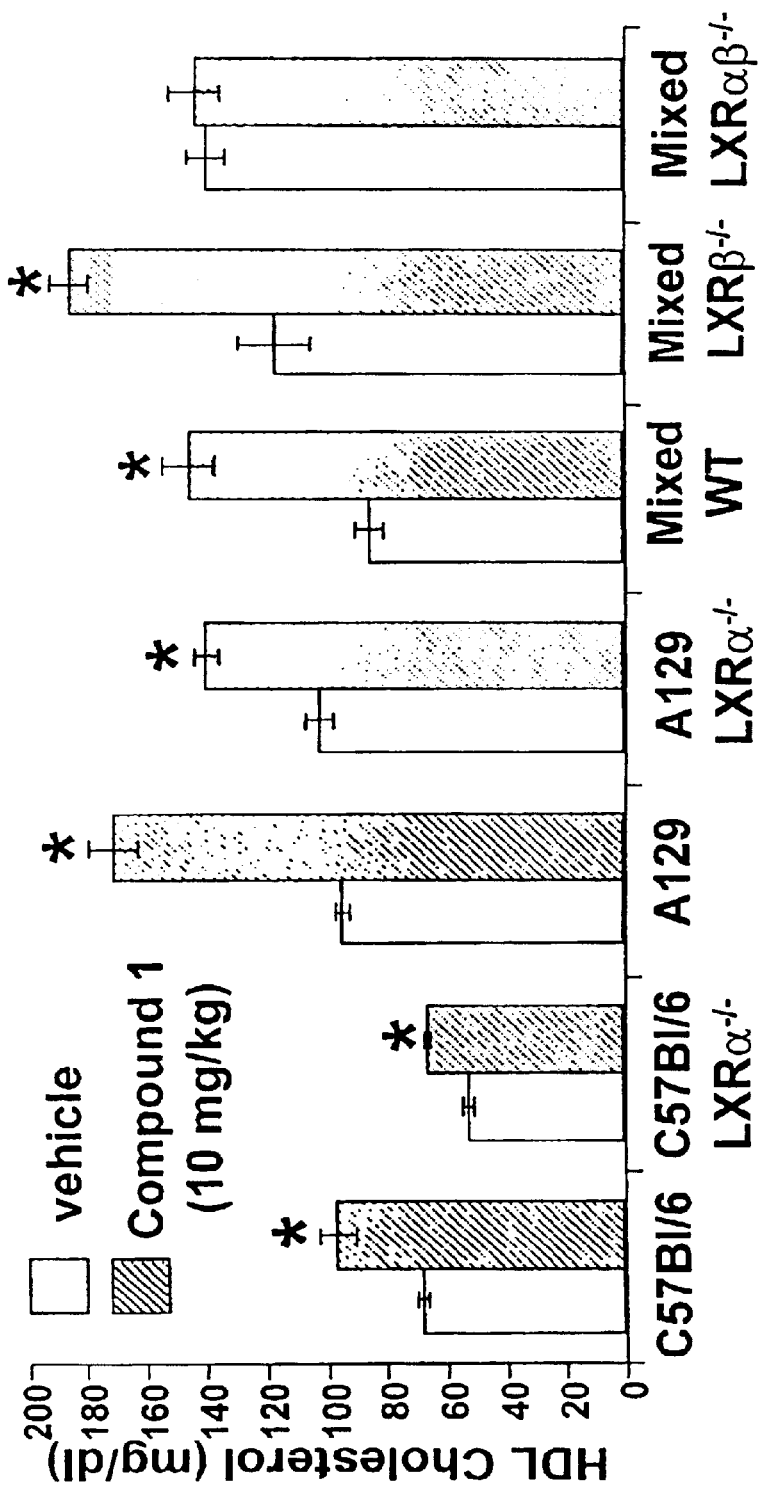
FIG. 5 illustrates the effect of the LXR pan-agonist Compound 1 on HDL cholesterol levels in wildtype, LXRα-/-, LXRβ-/-, and LXRαβ-/- mice. Compound 1 (10 mg/kg) was dosed daily for seven days by oral gavage. HDL levels were determined from plasma samples taken on day 7. Data presented is the average value derived from seven animals in each group except for LXRα$^{-/-}$/C57BL/6 which is the average of six animals. (+Compound 1/Vehicle, hatched bars; vehicle only, white bars.) *Signifies that the value is statistically different from the vehicle treated value within each genotype.

To determine the individual contribution of LXRα and LXRβ to increases in HDL cholesterol levels, Compound 1 (10 mg/kg) was administered for seven days by daily oral gavage in a sesame oil/ethanol vehicle via a 1 cc syringe fitted with a 20G disposable feeding needle. Compound was solvated in ethanol (5% final volume) and brought up to final volume with sesame oil (Sigma, St. Louis, Mo.). On day 7 mice were anesthetized with isofluorane and blood samples were obtained by retro-orbital plexus puncture. Blood samples were collected in heparinized tubes, centrifuged to obtain plasma and stored at -20° C. HDL levels were determined by precipitating non-HDL cholesterol from plasma samples using a precipitating reagent (Wako Diagnostic 278-67409, Richmond, Va.). The remaining HDL cholesterol was than quantitated using a colorimetric enzymatic assay adapted to a 96 well plate format (Infinity Total Cholesterol Reagent, Sigma, St. Louis, Mo.). As shown in FIG. 5, treatment of wildtype mice with an LXR pan-agonist results in a significant increase in HDL levels. The LXR panagonist-dependent increase in HDL is slightly reduced upon elimination of LXRα in either the C57BL/6 (8%) or A129 (23%) strains and unchanged when LXRβ is eliminated. As expected the agonist-dependent HDL is completely lost in LXRαβ-/- animals. Thus either LXRα or LXRβ alone is competent to elevate HDL cholesterol in response to agonist treatment (FIG. 5). The lack of selectivity in HDL regulation contrasts the selective decrease in triglyceride levels observed only when LXRα is eliminated (LXRα-/-, LXRαβ-/-; FIGS. 1 and 2).

Figure 6:
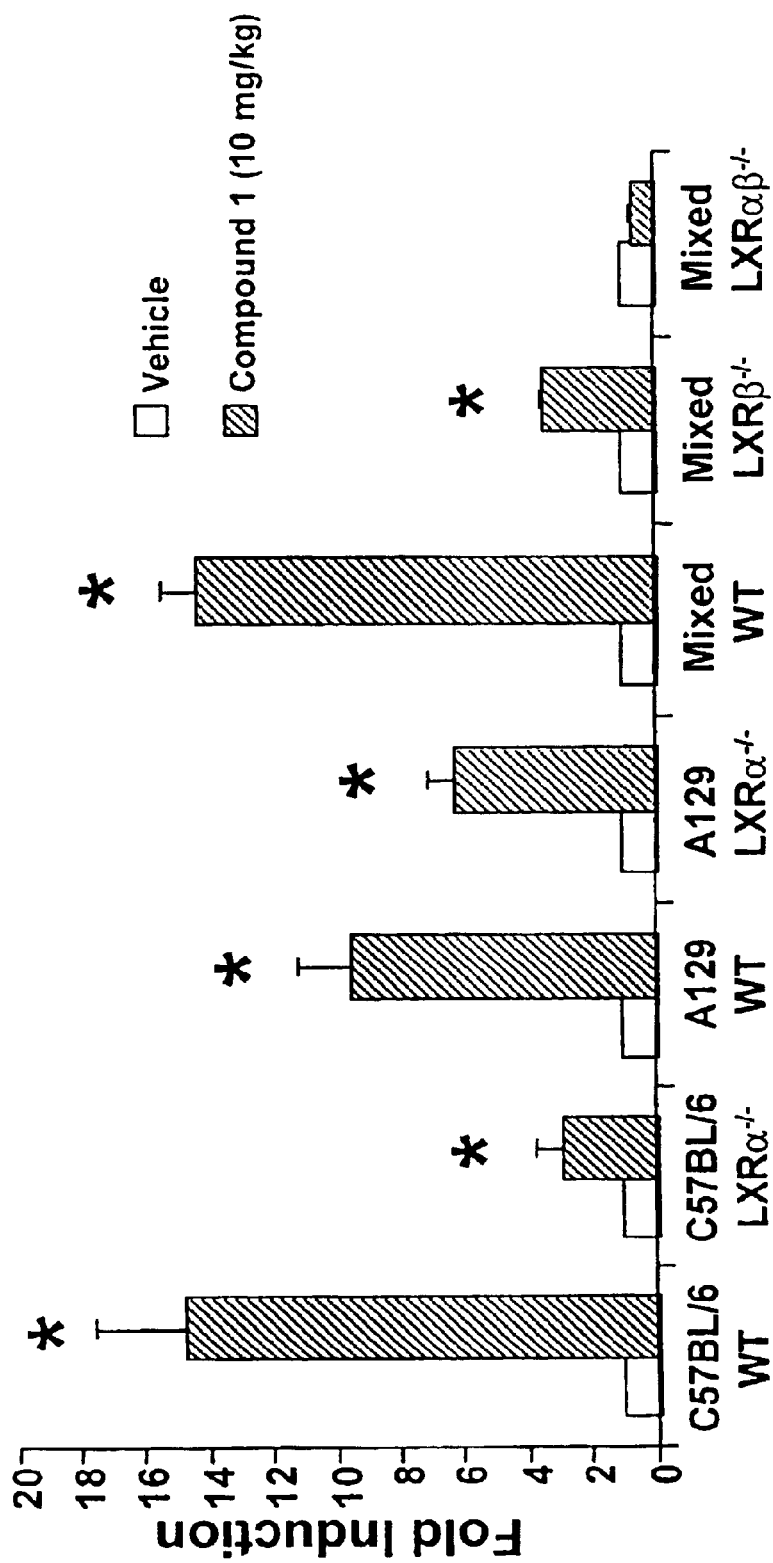
FIG. 6 illustrates the effect of the LXR pan-agonist Compound 1 on CYP7a mRNA levels in wildtype, LXRα-/-, LXRβ-/-, and LXRαβ-/- mice. Compound 1 (10 mg/kg) was dosed daily for seven days by oral gavage. CYP7a levels were measured by quantitative PCR of total liver RNA. Data is expressed as fold induction by Compound 1 (+Compound 1/Vehicle, hatched bars). The value for vehicle treated mice in each group was set at 1.0 (white bars). Data is the average of four animals per group assayed in triplicate. *Signifies that the value is statistically different from the vehicle treated value within each genotype.

The CYP7a gene encodes cholesterol 7α-hydroxylase, the rate-limiting enzyme in the catabolic conversion of cholesterol to bile acids. Increases in CYP7a activity stimulate the conversion of cholesterol to bile acids and may reduce plasma cholesterol levels by depleting hepatocytes of cholesterol. Intracellular cholesterol depletion should stimulate the uptake of LDL particles from the plasma by liver hepatocytes. To determine the contribution of LXRα and LXRβ to the induction of CYP7a by LXR agonists, Compound 1 was administered for seven days by daily oral gavage in a sesame oil/ethanol vehicle via a 1-cc syringe fitted with a 20G disposable feeding needle. Compound was solvated in ethanol (5% final volume) and brought up to final volume with sesame oil (Sigma, St. Louis, Mo.). Three hours after the final dose (day 7) animals were sacrificed, livers were harvested, and total liver RNA was isolated using RNeasy kits (QIAGEN Inc.) according to the supplier's total RNA isolation procedure. The RNA samples were further treated with deoxyribonuclease 1 to eliminate contaminating genomic DNA. CYP7a mRNA levels were than analyzed by real-time based quantitative PCR using Perkin Elmer ABI Prism 7700 and Sequence Detection System software (Perkin Elmer). The data in FIG. 6 indicate that LXR agonists can induce transcription of the CYP7a gene in wildtype, LXRα-/-, and LXRβ-/- mice. As expected no induction is observed in LXRαβ-/- mice. The data indicate that LXRβ alone is sufficient to induce CYP7a in response to agonist treatment to levels that are 20%–50% of that observed in wildtype agonist-treated mice.

Figure 7:
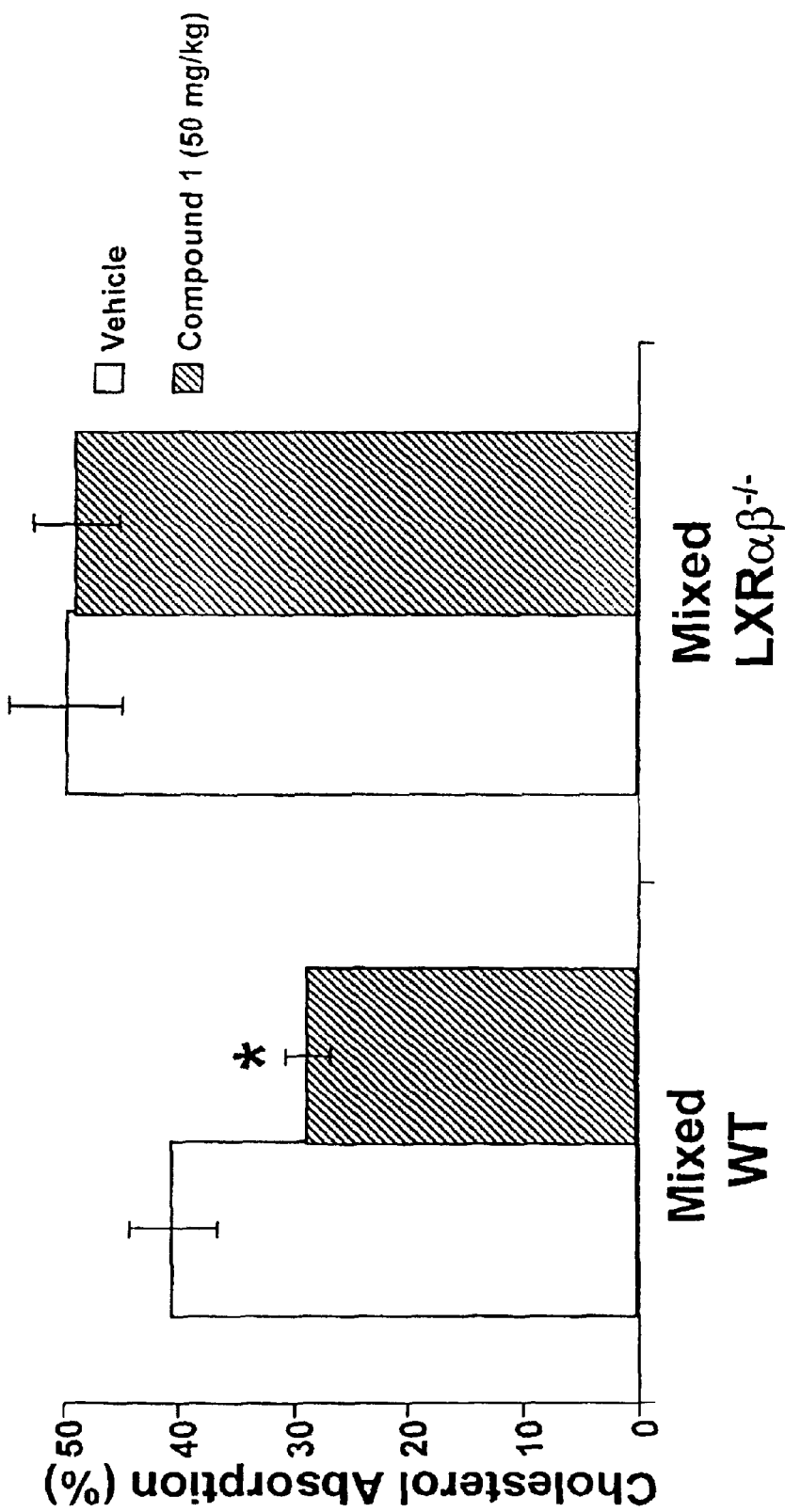
FIG. 7 illustrates the effect of the LXR pan-agonist Compound 1 on dietary cholesterol absorption. Compound 1 (50 mg/kg) was dosed daily for seven days by oral gavage. Cholesterol absorption was than measured using the fecal extraction method. Data is expressed as the percentage of radiolabeled cholesterol that was absorbed and is the average of seven animals in each group. (+Compound 1/Vehicle, hatched bars; vehicle only, white bars.) *Signifies that the value is statistically different from the vehicle treated control value.

Induction of cholesterol efflux pumps such as ABCA1 in the intestine limits the absorption of dietary cholesterol by stimulating the efflux of cholesterol out of intestinal enterocytes and into the intestinal lumen where it is excreted. To examine the effect of LXR pan-agonists on dietary cholesterol absorption, mixed wildtype and LXRαβ–/– mice were treated with vehicle or Compound 1 (50 mg/kg) for seven days prior to the initiation of the cholesterol absorption protocol. Compound 1 was administered by daily oral gavage in a 1% carboxy methyl-cellulose/ethanol vehicle via a 1-cc syringe fitted with a 20G disposable feeding needle. Compound was solvated in ethanol (5% final volume) and brought up to final volume with 1% carboxy methylcellulose. On day seven of the study, animals received a single oral bolus dose of 0.67 μCi [4-$^{14}$C]cholesterol (New England Nuclear, Boston, Mass.) and 1.3 μCi [5,6-$^3$H] sitostanol (ARC, St. Louis Mo.) by gavage in MCT oil (Mead Johnson, Evansville, Ind.). Feces were collected for 24 hours, ground to a fine powder and cholesterol was extracted using Folch (2:1 chloroform:methanol) followed by petroleum ether. Extracted samples were counted on a scintillation counter and then analyzed based upon the following equation. $[((^{14}C/^3H)$ dosing mixture$)-(^{14}C/^3H)$ fecal samples$)]/((^{14}C/^3H)$ dosing mixture$)$. As shown in FIG. 7, treatment of mixed wildtype animals with Compound 1 results in a significant decrease in cholesterol absorption. This agonist-dependent effect is lost in LXRαβ–/– mice indicating a requirement for LXR activity in mediating this activity.

Figure 8:
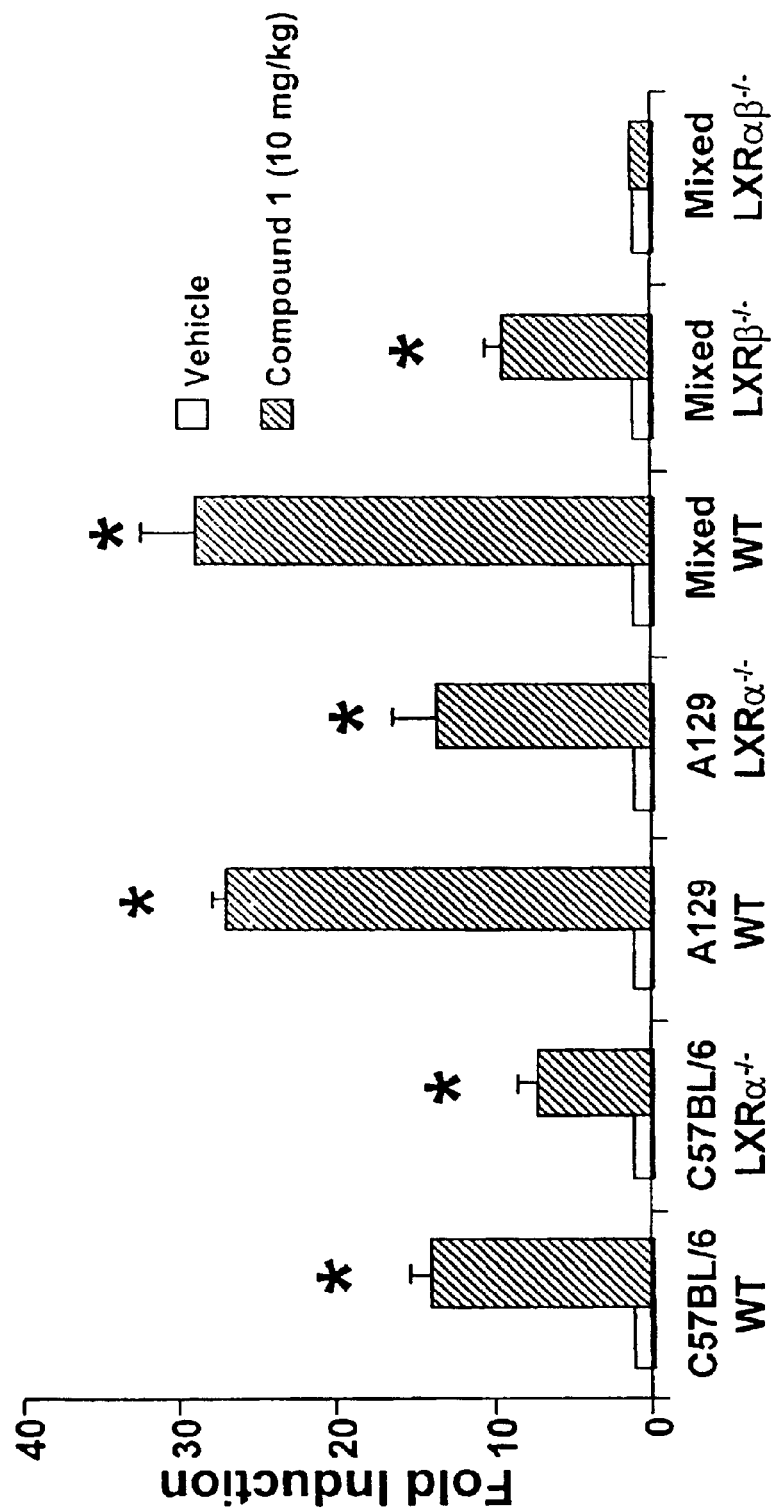
FIG. 8 illustrates the effect of the LXR pan-agonist Compound 1 on ABCA1 mRNA levels in the intestines of wildtype, LXRα-/-, LXRβ-/-, and LXRαβ-/- mice. Compound 1 (10 mg/kg) was dosed daily for seven days by oral gavage. ABCA1 levels were measured by quantitative PCR of total intestinal mucosa RNA. Data is expressed as fold induction by Compound 1 (+Compound 1/Vehicle, hatched bars). The value for vehicle treated mice in each group was set at 1.0 (white bars). Data is the average of four animals per group assayed in triplicate. *Signifies that the value is statistically different from the vehicle treated value within each genotype.

The LXR pan-agonist-dependent inhibition of cholesterol absorption is believed to result from the ability of LXRs to induce the expression of ATP binding cassette transporters such as ABCA1 in the intestine. To examine the contributions of LXRα and LXRβ to intestinal gene expression and dietary cholesterol absorption, Compound 1 was administered to wildtype, LXRα–/–, LXRβ–/– and LXRαβ–/– mice for seven days by daily oral gavage in a sesame oil/ethanol vehicle via a 1 cc syringe fitted with a 20G disposable feeding needle. Compound was solvated in ethanol (5% final volume) and brought up to final volume with sesame oil (Sigma, St. Louis, Mo.). Three hours after the final dose (day 7) animals were sacrificed, intestines were harvested, and intestinal enterocytes were isolated by gently scraping the mucosa layer away from the rest of the tissue. Total intestinal mucosa RNA was isolated using RNeasy kits (QIAGEN Inc.) according to the supplier's total RNA isolation procedure. The RNA samples were further treated with deoxyribonuclease I to eliminate contaminating genomic DNA. ABCA1 mRNA levels were than analyzed by real-time based quantitative PCR using Perkin Elmer ABI Prism 7700 and Sequence Detection System software (Perkin Elmer). The data in FIG. 8 demonstrate a dramatic induction of ABCA1 in the intestine of wildtype (14–29 fold depending on the strain), LXRα–/– (7–14 fold depending on the strain) and LXRβ–/– (9 fold) mice. No induction is observed in LXRαβ–/– mice. Thus either LXRα or LXRβ alone is sufficient to induce ABCA1 in the intestine and inhibit the absorption of dietary cholesterol.

Accumulation of cholesterol by macrophages present in artery walls plays a major role in the formation of atherosclerotic lesions and cardiovascular disease. Mice in which apolipoprotein E (ApoE) or the low density lipoprotein receptor (LDLR) has been genetically inactivated (ApoE–/– and LDLR–/–) are well established mouse models of atherosclerosis. ApoE–/– mice spontaneously develop high levels of atherosclerosis while LDLR–/– mice develop high levels of atherosclerosis only when placed on a high fat diet. To determine the contribution of LXR activity to atherosclerosis, bone marrow transplantation experiments were used to eliminate LXRα and LXRβ activity in the macrophages of ApoE–/– and LDLR–/– mice. Recipient female ApoE–/– and LDLR–/– mice (8–12 weeks of age) housed in microisolator cages were lethally irradiated with 900 rads (9 Gy) from a cobalt γ-source. Lethally irradiated recipient mice were rescued from death by transplantation with 5×10$^6$ bone marrow cells from wildtype or LXRαβ–/– mice. Bone marrow cells were harvested from 6–8 week old donor mice by flushing tibia and femurs with RPMI 1640 medium (Life Technologies) containing 10% fetal bovine serum (FBS), 2 mmol/L glutamine, 100 μg/mL streptomycin and 100 IU penicillin (Life Technologies) and heparin 5 units/mL. Bone marrow cells were washed, resuspended in fresh medium, counted, and introduced into recipients via tail vein injection within 6 hrs after irradiation. Repopulation of irradiated ApoE–/– and LDLR–/– mice with ApoE–/– and LDLR–/– derived bone marrow respectively served as additional controls. Since macrophages are derived from bone marrow precursors, this experimental paradigm allows creation of animals that have LXRα and LXRβ selectively eliminated in macrophages. After transplantation, animals were maintained on a normal chow diet for 8 weeks (ApoE–/– study) or on a high fat diet for five weeks (LDLR–/– study).

Figure 9:
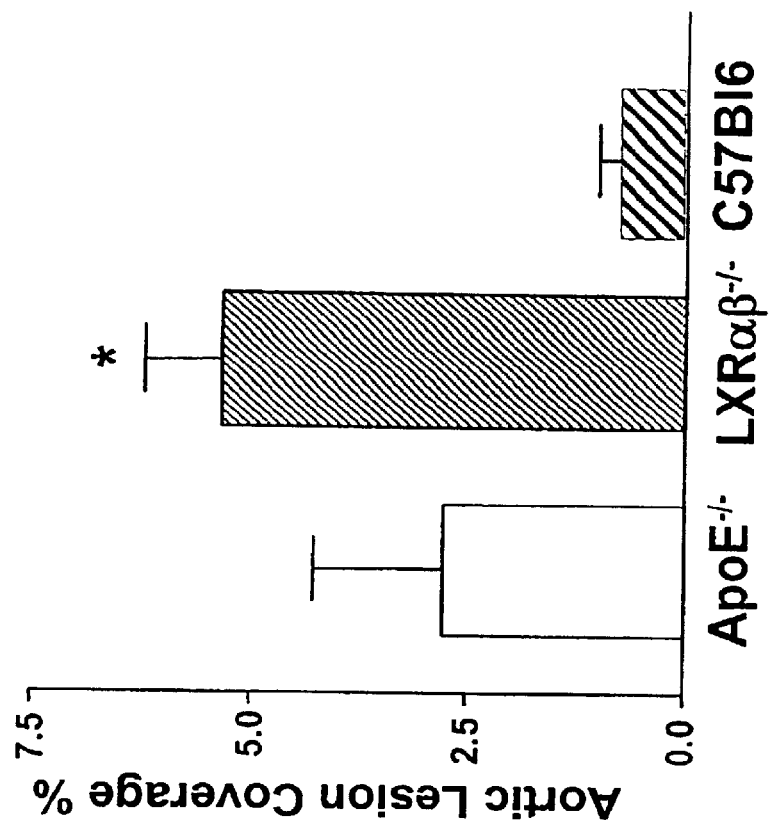
FIG. 9A shows representative sudan IV stained en fase aorta preparations from ApoE-/- mice following LXRαβ-/- bone marrow transplants. Atherosclerotic lesions stain red.
FIG. 9B illustrates the effects of LXRαβ-/- bone marrow transplants on ApoE-/- mice via quantitation of the surface area of aortas covered with lesions. Data is the average of six aortas for the ApoE-/- to ApoE-/- group and seven aortas for the wildtype to ApoE-/- and LXRαβ-/- to ApoE-/- groups. *Signifies that the value is statistically different from the ApoE-/- to ApoE-/- control bone marrow transplant value.
Figure 9:
Figure 10B:
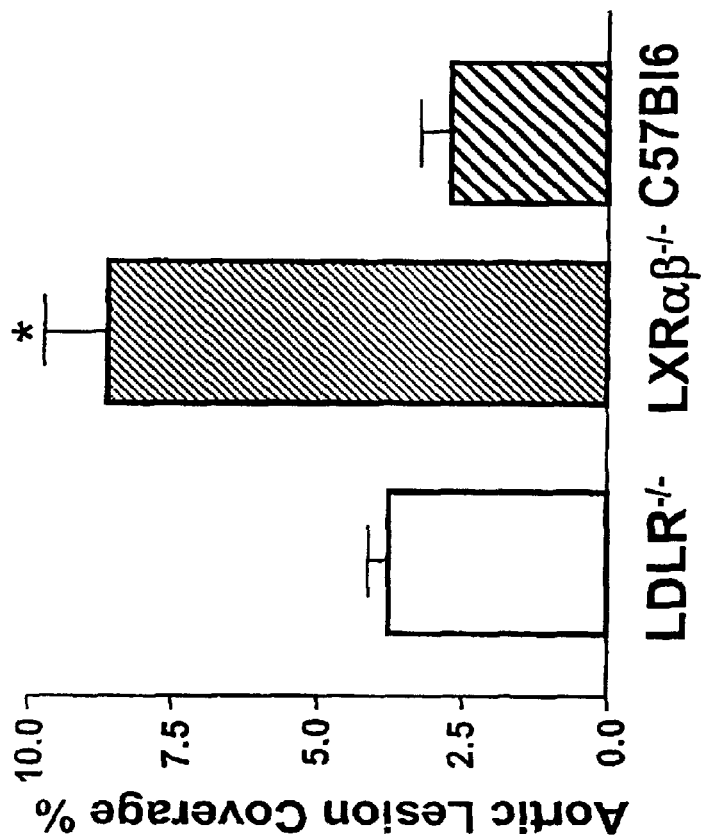
FIG. 10B illustrates the effects of LXRαβ-/- bone marrow transplants on LDLR-/- mice via quantitation of the surface area of aortas covered with lesions. Data is the average of seven aortas for the LDLR-/- to LDLR-/- group, 11 aortas in the wildtype to LDLR-/- group, and 12 aortas in the LXRαβ-/- to LDLR-/- group. *Signifies that the value is statistically different from the LDLR-/- to LDLR-/- control bone marrow transplant value.
Figure 10A:
FIG. 10A shows representative sudan IV stained en face aorta preparations from LDLR-/- mice following LXRαβ-/- bone marrow transplants. Atherosclerotic lesions stain red.

To quantitate atherosclerosis in transplanted animals the extent of atherosclerosis in en face mouse aortic preparations was determined. Mice were sacrificed by carbon dioxide inhalation and aortas were immediately perfused with ice cold phosphate buffered saline (PBS) by inserting a canula into the left ventricle. Heart and aortas were then exposed by careful dissection of adventitial fat and surrounding tissue. Aortas extending from the aortic root to the iliac bifurcation were cut out and fixed, opened longitudinally to obtain a flat preparation, stained with Sudan IV and pinned out for visualization. The extent of atherosclerosis in en face aortic preparations was quantitated by computer-assisted image analysis. Digitized 24-bit color images of Sudan IV-stained aortas were captured with a Polaroid Camera connected to a Leica MZ 12 microscope. The digitized images were analyzed using Image Pro Plus image analysis software (Media Cybernatics). The lesion areas covering the aortic surface analyzed using the program were expressed as percent of the entire aortic surface area. The results of this analysis (FIG. 9 and FIG. 10) demonstrated that elimination of LXRα and LXRβ in macrophages increases the extent of atherosclerosis in both the ApoE–/– (8 fold compared to wildtype controls, FIG. 9) and LDLR–/– (4 fold compared to wildtype controls, FIG. 10) models. Thus together LXRα and LXRβ function to inhibit atherosclerosis and can be considered anti-atherogenic factors.

Figure 11:
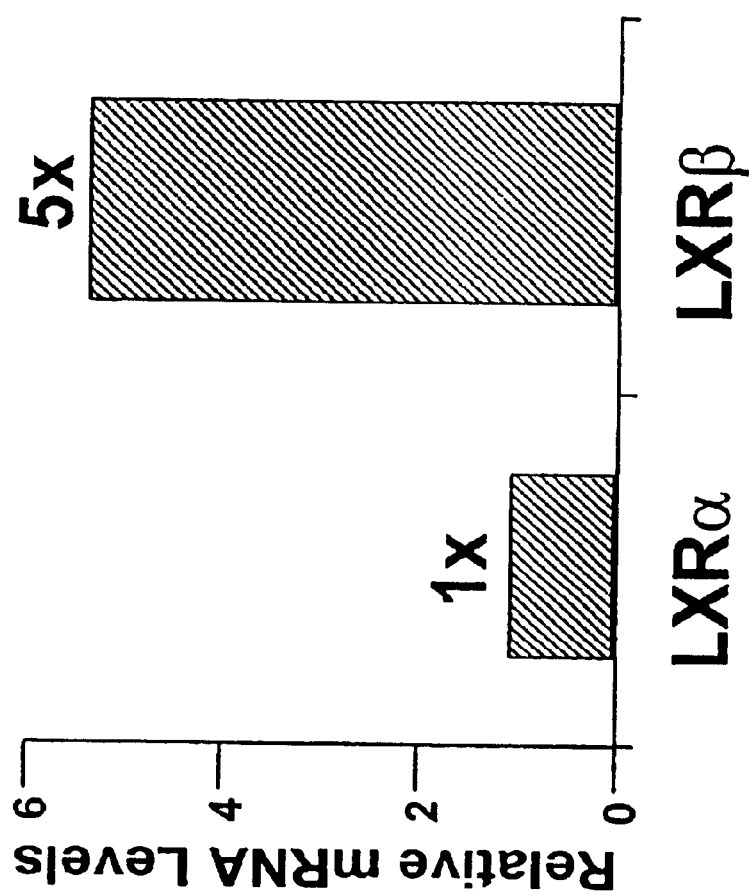
FIG. 11 illustrates the relative mRNA levels for LXRα and LXRβ in peritoneal macrophages isolated from mixed wildtype mice. Peritoneal macrophages were cultured in vitro for 24 hours, total RNA was isolated and the levels of the LXRα and LXRβ mRNAs were determined by quantitative PCR. The value for LXRα was set at one. Value is the average of three samples assayed in triplicate.

The individual contributions of both receptors to macrophage gene expression were examined by first measuring the amount of mRNA encoding LXRα and LXRβ in thioglycolate-elicited peritoneal macrophages obtained from mixed wildtype mice. Thioglycolate-elicited peritoneal macrophages were isolated from mice 4 days after peritoneal injection of thioglycolate media. Peritoneal macrophages were harvested by lavage of the peritoneum with phosphate buffered saline (PBS), cells were washed, transferred to 60 mm culture plates and incubated at 37° C. in RPMI 1640 media (Life Technologies) containing 10% FBS, 2 mmol/L glutamine, 100 μg/mL streptomycin and 100 IU penicillin (Life Technologies). After 5 hours at 37° C., cells were washed 5 times with PBS to remove non-adherent cells and adherent cells were further incubated in RPMI 1640 media supplemented with 10% FBS for 24 hours. To determine the mRNA levels of LXRα and LXRβ, after 24 hours total RNA was isolated from cultured macrophages using RNeasy kits (QIAGEN Inc.) according to the supplier's total RNA isolation procedure. The RNA samples were further treated with deoxyribonuclease I to eliminate contaminating genomic DNA. LXRα and LXRβ mRNA levels were than analyzed by real-time based quantitative PCR using Perkin Elmer ABI Prism 7700 and Sequence Detection System software (Perkin Elmer). FIG. 11 indicates that there is five times more LXRβ mRNA present in macrophages compared to the levels for LXRα, indicating that LXRβ is the relatively more important regulator of LXR-dependent gene expression in this cell-type.

Figure 12:
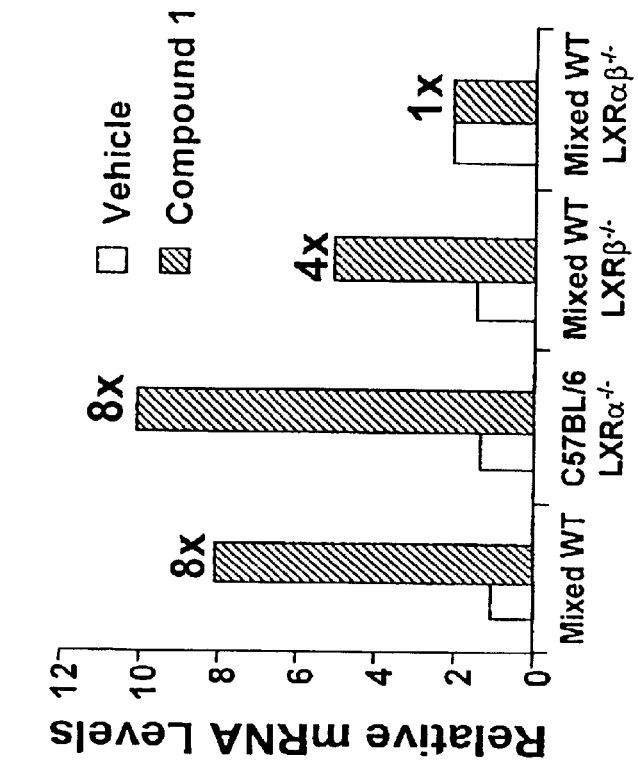
FIG. 12A illustrates the effect of the LXR pan-agonist Compound 1 on ABCA1 mRNA levels in peritoneal macrophages isolated from mixed wildtype. LXR-/- (C57BL/6). LXRβ-/-, and LXRαβ-/- mice. Peritoneal macrophages were cultured in vitro for 24 hours in the absence (white bars) or presence (hatched bars) of 1.0 μM Compound 1, total RNA was isolated and the levels of the ABCA1 mRNA were determined by quantitative PCR. Values reported are the averages of three samples for each group assayed in triplicate. Numbers above the hatched bars are the values for the fold induction by Compound 1 (+Compound 1/Vehicle).
FIG. 12B illustrates the effect of the LXR pan-agonist Compound 1 on ABCG1 mRNA levels in peritoneal macrophages isolated from mixed wildtype. LXRα-/- (C57BL/6). LXRβ-/-, and LXRαβ-/- mice. Peritoneal macrophages were cultured in vitro for 24 hours in the absence (white bars) or presence (hatched bars) of 1.0 μM Compound 1, total RNA was isolated and the levels of the ABCG1 mRNA were determined by quantitative PCR. Values reported are the averages of three samples for each group assayed in triplicate. Numbers above the hatched bars are the values for the fold induction by Compound 1 (+Compound 1/Vehicle).
Figure 12:
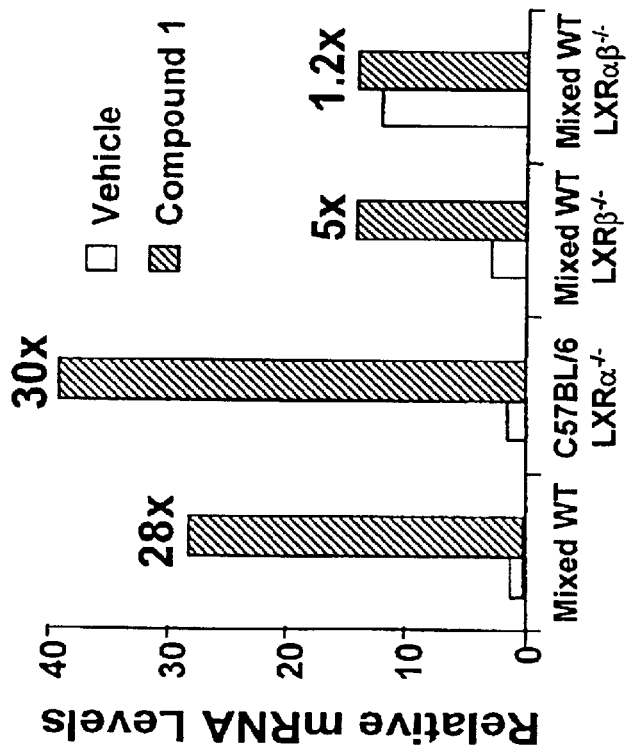

To further examine LXR-dependent gene expression in macrophages, peritoneal macrophages were isolated as described above from mixed wildtype, LXRα-/- (C57BL/6), LXRβ-/-, and LXRαβ-/- mice. After removal of non-adherent cells, the remaining macrophages were than cultured in either the absence or presence of LXR pan-agonist (1.0 μM Compound 1) for 24 hours. At the end of the experiment total RNA was isolated from cultured macrophages using RNeasy kits (QIAGEN Inc.) according to the supplier's total RNA isolation procedure. RNA samples were further treated with deoxyribonuclease I to eliminate contaminating genomic DNA before use. The LXR agonist-dependent induction of the ABCA1 and ABCG1 mRNAs were than analyzed by real-time based quantitative PCR using Perkin Elmer ABI Prism 7700 and Sequence Detection System software (Perkin Elmer). ABCA1 and ABCG1 function as efflux pumps that mediate the transfer of intracellular cholesterol out of cells to HDL particles, a process referred to as reverse cholesterol transport. As shown in FIG. 12, treatment of wildtype cells results in a 28 fold induction of the ABCA1 mRNA (Panel A) and an 8 fold induction of ABCG1 (Panel B) mRNAs. Elimination of LXRα activity (LXRα-/-) has no effect on the agonist-dependent response. In contrast, elimination of LXRβ activity (LXRβ-/-) reduces the agonist-dependent induction of ABCA1 by 82% and the ABCG1 induction by 50%. As expected elimination of both receptors completely blocks the response. Thus LXRβ alone is sufficient to allow the maximum induction of ABCA1 and ABCG1 in peritoneal macrophages.

Figure 13:
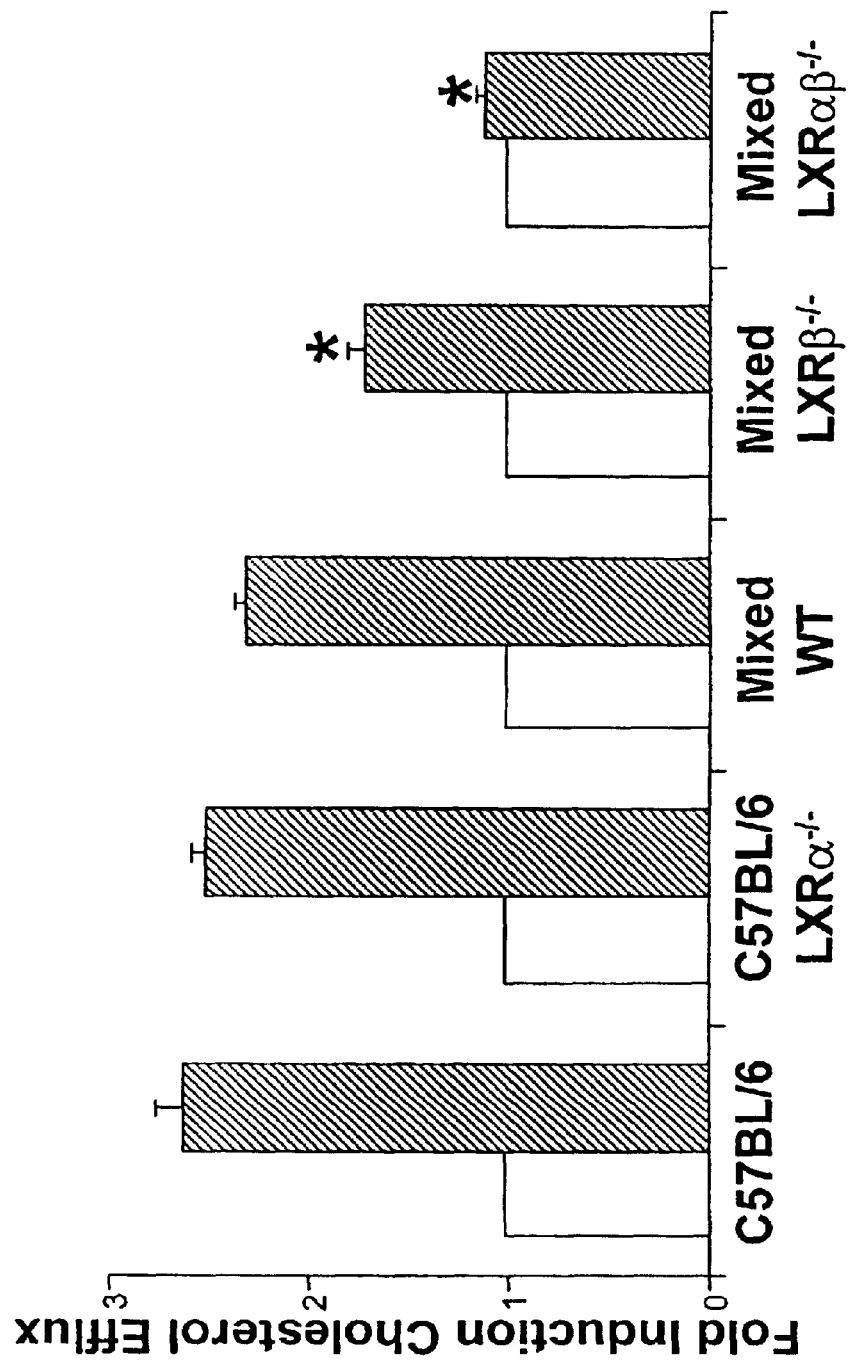
FIG. 13 illustrates the effect of the LXR pan-agonist Compound 1 on cholesterol efflux in peritoneal macrophages isolated from wildtype (mixed and C57BL/6), LXRα-/- (C57BL/6), LXRβ-/-, and LXRαβ-/- mice. Peritoneal macrophages were cultured in vitro for 24 hours, cells were labeled with $^{14}$C-cholesterol and cultured for an addition 24 hours in the absence (white bars) or presence (hatched bars) of 1.0 μM Compound 1 to measure cholesterol efflux. Data is expressed as fold induction by Compound 1 (+Compound 1/Vehicle, hatched bars). The value for vehicle treated cells in each group was set at 1.0 (white bars). Data is the average of three samples per group assayed in triplicate. *Signifies that the value is statistically different from the wildtype control value.

Since ABCA1 is involved in mediating reverse cholesterol transport, peritoneal macrophages isolated as described above and cultured for 24 hours in the absence or presence of LXR agonist (1.0 μM Compound 1) were examined in a cholesterol efflux assay which measures reverse cholesterol transport in vitro. Mouse peritoneal macrophages isolated as described above from wildtype (mixed and C57BL/6), LXRα-/- (C57BL/6), LXRβ-/-, and LXRαβ-/- mice were cultured in 96 well plates ($5 \times 10^4$ cells/well) at 37° C. After 24 hours, cells were labeled for 48 hours with 0.2 μCi/ml $^{14}$C-cholesterol in RPMI 1640 medium with 1% FBS. Following the labeling period, $^{14}$C-cholesterol was removed and the cells were cultured for 24 hours in serum free RPMI 1640 media in the presence or absence of 10 μg/ml apolipoprotein A (ApoA1). In this assay ApoA1 acts as a cholesterol acceptor and mimics the cholesterol-accepting function performed by HDL particles in vivo. Following this incubation, the media is removed, cells are washed and than lysed with 0.2 M sodium hydroxide. To determine ApoA1-dependent cholesterol efflux, the amount of $^{14}$C-cholesterol present in the media is divided by the total counts (media+ cell lysate) and the value determined in the absence of ApoA is subtracted from the value determined in the presence of ApoA. As shown in FIG. 13, in peritoneal macrophages the LXR pan-agonist stimulates reverse cholesterol transport in wildtype (mixed and C57BL/6) cells. However, reverse cholesterol transport is significantly reduced upon elimination of LXRβ and further reduced when both receptors are eliminated. No effect is observed upon elimination of LXRα alone.

The results of in vitro and in vivo experiments indicate that an LXRβ selective agonist will provide effective treatment for atherosclerosis and cardiovascular disease by stimulating reverse cholesterol transport and increasing HDL levels, by promoting the metabolic conversion of cholesterol to bile acids, and by inhibiting the absorption of dietary cholesterol. The therapeutic value of such an LXRβ-selective agonist will be greater than that of LXR pan-agonists or LXRα-selective agonists because such compounds will elevate plasma triglycerides which has been shown to increase the risk of cardiovascular disease.

To further evaluate the long-term effects of macrophage LXR deficiency in vivo, recipient male LDLR-/- mice (8–12 weeks of age) housed in microisolator cages were lethally irradiated with 900 rads (9 Gy) from a cobalt resource. Lethally irradiated recipient LDLR-/- mice were rescued from death by transplantation with $5 \times 10^6$ bone marrow cells from wildtype, LXRα-/-, LXRβ-/-, or LXRαβ-/- mice. Bone marrow cells were harvested from 6–8 weeks old donor mice by flushing tibia and femurs with RPMI 1640 medium (Life Technologies) containing 10% fetal bovine serum (FBS), 2 mmol/L glutamine, 100 μg/mL streptomycin and 100 IU penicillin (Life Technologies) and heparin 5 units/mL. Bone marrow cells were washed, resuspended in fresh medium, counted, and introduced into recipients via tail vein injection within 6 hours after irradiation. After transplantation, animals were maintained on a high fat diet for 20 weeks.

Figure 14:
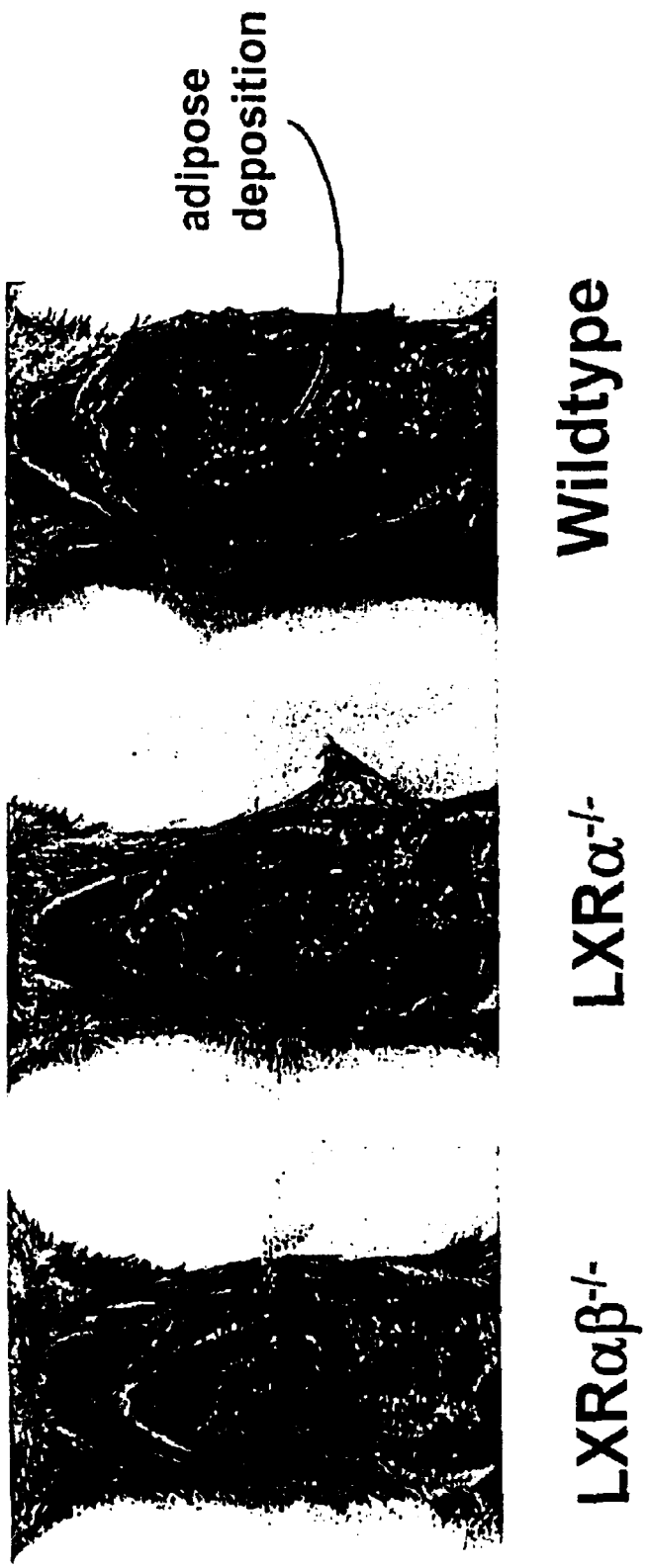
FIG. 14 demonstrates the reduced adipose mass in LDLR-/- bone marrow recipients that have received from bone marrow from LXRα-/- or LXRαβ-/- mice. Photomicrographs were taken at necropsy after 20 weeks on a high fat diet.

At necropsy a dramatic difference in adipose mass was observed when mice from each group were examined (FIG. 14). As expected, LDLR-/-recipient mice that have received bone marrow from wildtype, LDLR-/-, or LXRβ-/-donor exhibit a large increase in adipose mass after 20 weeks on a high fat diet. In comparison, however, LDLR-/-recipient mice that had received bone marrow from LXRα-/- or LXRαβ-/- mice have far less adipose tissue (FIG. 14). The ability of LXRα activity to selectively modulate adipogenesis has important implications for the use of LXR ligands as therapeutic agents. First, since elimination of LXRα activity inhibits the diet-induced gain in adipose mass, increasing the activity of LXRα with a pan-agonist or a LXRα-selective agonist promotes adipose deposition. Since elimination of LXRβ alone does not influence the gain in adipose mass, a LXRβ-selective agonist will not have this unwanted side effect. Second, since genetically eliminating LXRα activity blocks diet-induced increases in adipose mass, a LXRα-selective antagonist has similar effects and thus, is an effective anti-obesity agent.

Cardiovascular disease is one of the major complications of type II diabetes. Interestingly, changes in lipid metabolism are also observed in type II diabetic patients. A mouse model of type II diabetes is the diabetic (db/db) mouse. [See Coleman, D. L. (1978), Obese and Diabetes: Two Mutant Genes Causing Diabetes-Obesity Syndrom In Mice. Diabetologia 14, 141–148; and Hong Chen, Olga Charlat, Louis A. Tartaglia, Elizabeth A. Woolf, Xun Weng, Stephen J. Ellis, Nathan D. Lakey, Janice Culpepper, Karen J. More, Roger E. Breitbart, Geoffrey M. Duyk, Robert I. and Jay P. Morgenstern (1996), Evidence That The Diabetes Gene Encodes The Leptin Receptor: Identification Of A Mutation In The Leptin Receptor In db/db Mice, Cell 84, 491–495.] Mice homozygous for this mutation are obese and exhibit severe hyperglycemia (elevated blood glucose), in contrast heterozygous littermates (db/+) are normal.

To examine the ability of LXR agonists to modulate blood glucose levels, db/db mice were treated for 14 days with 50 mg compound/kg body weight of the LXR agonist Compound 1. As a positive control animals were also treated with 30 mg compound/kg body weight of the retinoid X receptor (RXR) agonist. RXR agonists such as 6-[1-(3-Fluoro-5,5,8, 8-tetramethyl-5,6,7,8-tetrahydro-napthalen-2-yl)-cyclopropyl]-nicotinic acid (Compound 2) are known antidiabetic agents and effectively lower blood glucose levels in db/db mice. Both compounds were administered by daily oral gavage in a sesame oil/ethanol vehicle via a 1-cc syringe fitted with a 20G disposable feeding needle. Compounds were solvated in ethanol (5% final volume) and brought up to final volume with sesame oil (Sigma, St. Louis, Mo.). Blood samples were collected before the first dose (day 0) and three hours after dosing on day 3, day 7, day 10 and day 14 into heparinized tubes. Samples were centrifuged to obtain plasma and stored at −20° C. Plasma glucose levels were determined using a colorimetric enzymatic assay adapted to a 96 well plate format (Sigma, St. Louis, Mo.). Sigma glucose standards (Sigma, St. Louis, Mo.) were use to generate standard curves. The absorbance of the samples and standards were read using a Multiskan plate reader. The results of this analysis (FIG. 15) demonstrate that the LXR agonist Compound 1 significantly reduces hyperglycemia in db/db mice and indicates LXR agonists provide effective therapy for the treatment of type II diabetes.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

Citation of the above documents is not intended as an admission that any of the foregoing is pertinent prior art, nor does it constitute any admission as to the contents or date of these documents.

We claim:

1. A method for treating diabetes in a mammal, said method comprising administering to said mammal a therapeutically-effective amount of an LXR agonist, wherein said treatment decreases hyperglycemia.

2. The method of claim 1 further comprising administering to said mammal a thiazolidinedione as an additional active agent.

3. The method of claim 1 wherein said LXR agonist is a pan LXR agonist.

4. The method of claim 1 wherein said LXR agonist is a LXRβ agonist.

5. The method of claim 4 wherein said LXRβ agonist is a partial agonist or agonist that exhibits about 2 to about 10 fold preference for LXRβ compared to LXRα.

6. The method of claim 1 wherein said agonist is in a composition comprising an additional active agent for treating diabetes.

7. The method of claim 6 wherein said active agent decreases hyperglycemia.

8. The method of claim 7 wherein said agent modulates diabetes or treats diabetes and its related symptoms, complications, and disorders.

9. The method of claim 1 wherein said agonist is N-(2, 2,2-trifluoroethyl)-N-[4-(2,2,2-trifluoro-1-hydroxy-1-trifluoromethylethyl)-phenyl]-benzene sulfonamide.

10. A method for treating type II diabetes in a mammal, said method comprising administering to said mammal a therapeutically-effective amount of an LXR agonist, wherein said treatment decreases hyperglycemia.

11. The method of claim 10 wherein said LXR agonist is a pan LXR agonist.

12. The method of claim 10 wherein said LXR agonist is a LXRβ agonist.

13. The method of claim 12 wherein said LXRβ agonist is a partial agonist or agonist that exhibits about 2 to about 10 fold preference for LXRβ compared to LXRα.

14. The method of claim 10 wherein said agonist is in a composition comprising an additional active agent for treating type II diabetes.

15. The method of claim 14 wherein said active agent decreases hyperglycemia.

16. The method of claim 15 wherein said agent modulates diabetes or treats diabetes and its related symptoms, complications, and disorders.

17. The method of claim 10 wherein said agonist is N-(2,2,2-trifluoroethyl)-N-[4-(2,2,2-trifluoro-1-hydroxy-1-trifluoromethylethyl)-phenyl]-benzene sulfonamide.

18. A method for treating type II diabetes in a mammal and reducing the cardiovascular complications of type II diabetes, said method comprising administering to said mammal a therapeutically-effective amount of an LXR agonist, wherein said treatment decreases hyperglycemia.

19. A method for decreasing hyperglycemia in a mammal comprising administering to said mammal a therapeutically-effective amount of an LXR agonist.

20. A method for treating diabetes in a mammal, said method comprising administering to said mammal a therapeutically-effective amount of an LXR agonist, wherein said treatment decreases insulin resistance.

21. A method for treating type II diabetes in a mammal, said method comprising administering to said mammal a therapeutically-effective amount of an LXR agonist, wherein said treatment decreases insulin resistance.

22. A method for treating type II diabetes in a mammal and reducing the cardiovascular complications of type II diabetes, said method comprising administering to said mammal a therapeutically-effective amount of an LXR agonist wherein said treatment decreases insulin resistance.

23. The method of claim 22 further comprising administering to said mammal a thiazolidinedione as an additional active agent.

24. A method for decreasing insulin resistance in a mammal comprising administering to said mammal a therapeutically-affective amount of an LXR agonist.

25. A method for improving the control of glucose homeostasis in a mammal, said method comprising administering to said mammal a therapeutically-effective amount of an LXR agonist, wherein the control of glucose homeostasis is improved by decreasing hyperglycemia or reducing insulin resistance.

* * * * *